(12) United States Patent  
Nara et al.

(10) Patent No.: US 8,301,289 B2  
(45) Date of Patent: Oct. 30, 2012

(54) DEFECT DETECTION METHOD OF DISPLAY DEVICE AND DEFECT DETECTION APPARATUS OF DISPLAY DEVICE

(75) Inventors: Kei Nara, Yokohama (JP); Tomohide Hamada, Yokohama (JP)

(73) Assignee: Nikon Corporation, Tokyo (JP)

( * ) Notice: Subject to any disclaimer, the term of this patent is extended or adjusted under 35 U.S.C. 154(b) by 319 days.

(21) Appl. No.: 12/753,517

(22) Filed: Apr. 2, 2010

(65) Prior Publication Data

US 2010/0256796 A1 Oct. 7, 2010

Related U.S. Application Data

(63) Continuation of application No. PCT/JP2008/002687, filed on Sep. 26, 2008.

(60) Provisional application No. 61/282,229, filed on Jan. 5, 2010.

(30) Foreign Application Priority Data

Oct. 5, 2007 (JP) ................................. 2007-261481

(51) Int. Cl.
*G06F 19/00* (2011.01)

(52) U.S. Cl. ......... 700/110; 700/108; 700/109; 382/149

(58) Field of Classification Search ............ 349/46, 349/54, 124, 155, 192; 348/29–30, 246; 345/3.3, 612, 616, 698; 438/30; 382/194, 382/149; 700/108–110; 445/24–25

See application file for complete search history.

(56) References Cited

U.S. PATENT DOCUMENTS

| | | | | |
|---|---|---|---|---|
| 5,032,536 | A | * | 7/1991 | Oritsuki et al. ................. 438/30 |
| 5,282,070 | A | * | 1/1994 | Nishida et al. ................ 349/111 |
| 5,546,206 | A | * | 8/1996 | Nakanishi et al. ............. 349/110 |
| 5,929,961 | A | | 7/1999 | Nishi et al. |
| 5,945,984 | A | * | 8/1999 | Kuwashiro .................... 345/206 |

(Continued)

FOREIGN PATENT DOCUMENTS

JP 08-190078 7/1996

(Continued)

OTHER PUBLICATIONS

Chinese Office Action, Application No. 200880110250.3, mailed Sep. 23, 2011.

(Continued)

*Primary Examiner* — Ramesh Patel
(74) *Attorney, Agent, or Firm* — Finnegan, Henderson, Farabow, Garrett & Dunner, L.L.P.

(57) ABSTRACT

A defect detecting method of a display device includes a defect counting process that measuring a feature amount for each partial region of a display device (P32), and counting regions which is determined as a defective portion based on the measured feature amount of the region (P36), a process that stopping a manufacturing line of the display device when a number of defects counted at the defect counting process is greater than a first threshold value (P38, P42), a defect density calculating process that calculating a defect density in a predetermined area when the number of defects counted at the defect counting process is smaller than the first threshold value (P38), and a process that stopping the manufacturing line of the display device when the defect density calculated at the defect density calculating process is higher than a second threshold value (P40, P42).

11 Claims, 14 Drawing Sheets

U.S. PATENT DOCUMENTS

| | | | |
|---|---|---|---|
| 7,718,912 B2* | 5/2010 | Akimoto | 209/576 |
| 2002/0130262 A1* | 9/2002 | Nakasuji et al. | 250/311 |
| 2005/0263810 A1* | 12/2005 | Iizuka et al. | 257/296 |
| 2007/0045536 A1* | 3/2007 | Nakasuji et al. | 250/310 |
| 2008/0121804 A1* | 5/2008 | Nakasuji et al. | 250/310 |

FOREIGN PATENT DOCUMENTS

| | | |
|---|---|---|
| JP | 09-160004 | 6/1997 |
| JP | 11-218466 | 8/1999 |
| JP | 2001-074600 | 3/2001 |
| JP | 2004-279239 | 10/2004 |
| JP | 2004-294202 | 10/2004 |
| JP | 3698749 B2 | 7/2005 |
| JP | 3698749 B2 | 9/2005 |

OTHER PUBLICATIONS

Written Opinion of the International Searching Authority with English language translation issued on the related PCT/JP2008/002687 on Dec. 22, 2008.

International Search Report, from the Japanese Patent Office in related International Application No. PCT/JP2008/002687, mailed Dec. 22, 2008.

* cited by examiner

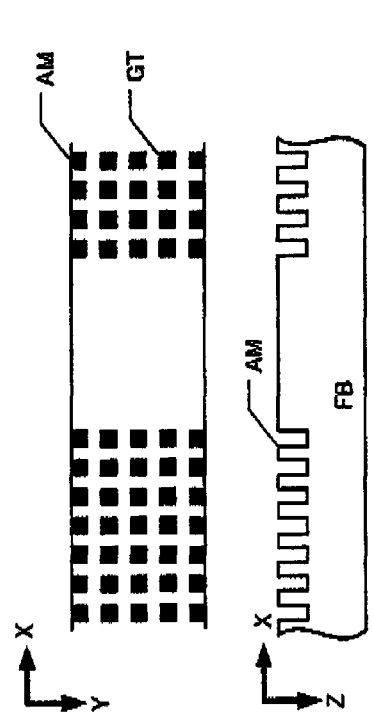
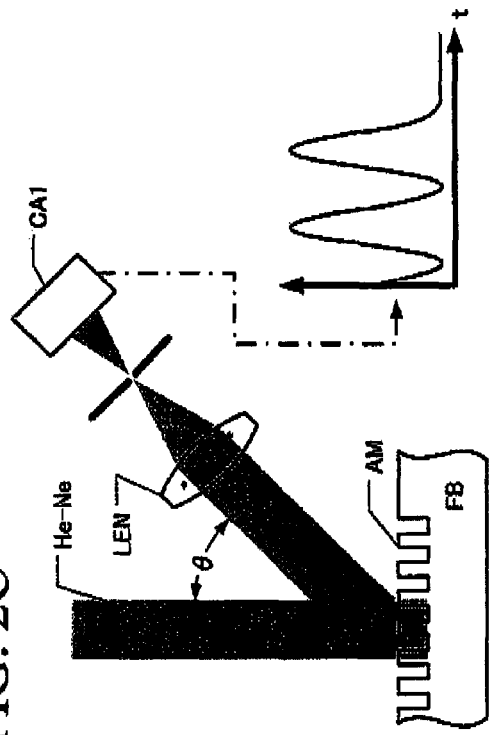
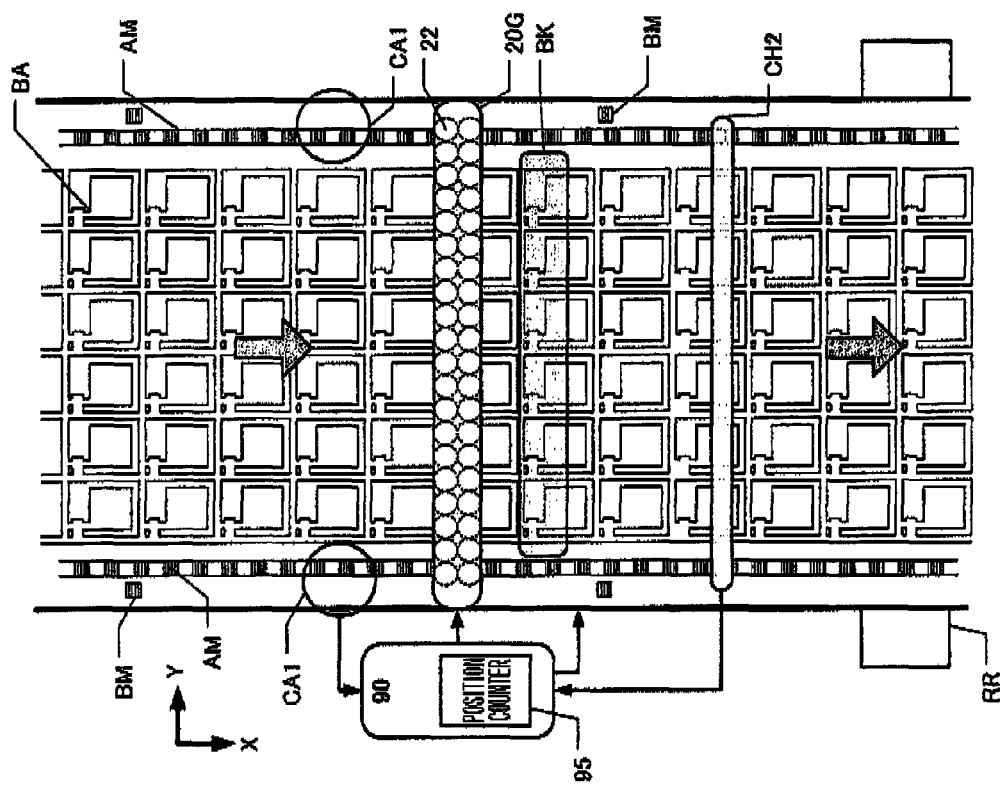
FIG. 2A
FIG. 2B
FIG. 2C

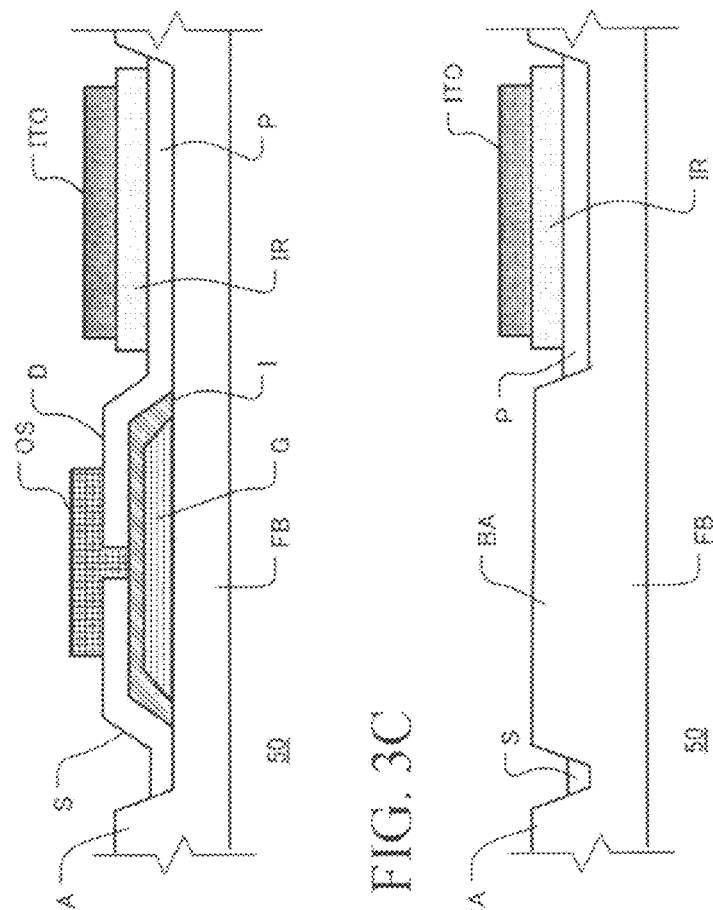
FIG. 3B
FIG. 3C
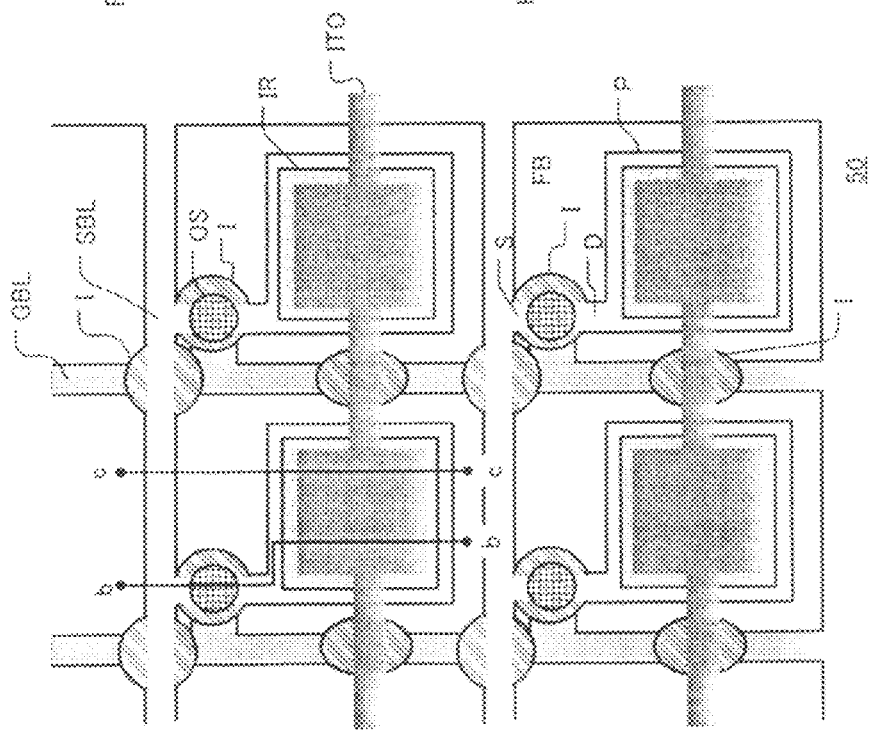
FIG. 3A

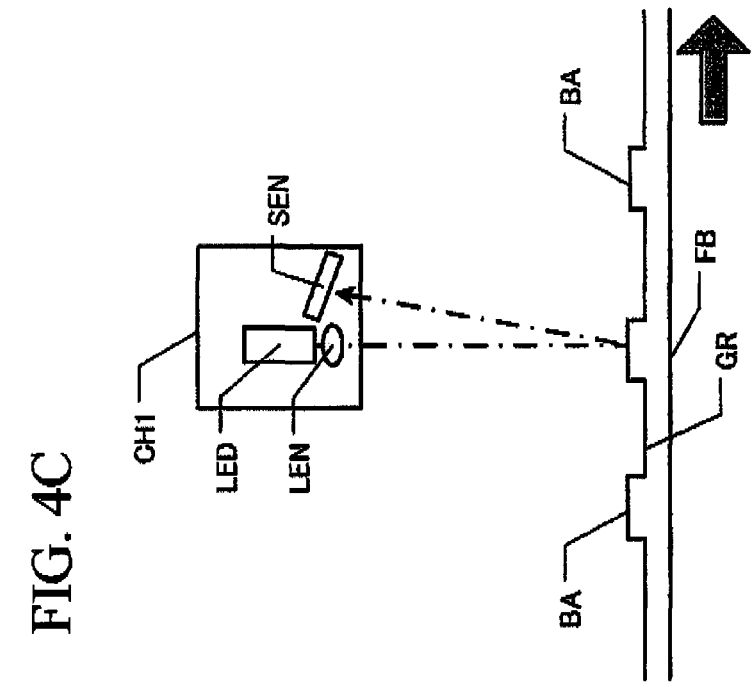
FIG. 4C
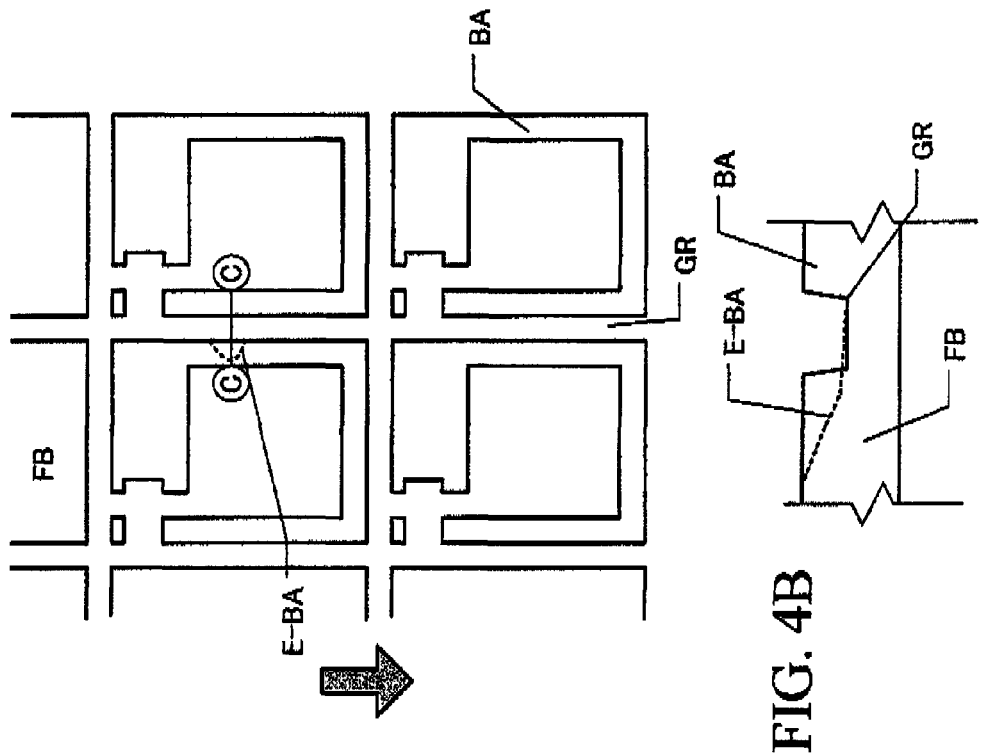
FIG. 4A
FIG. 4B

DEFECT DETECTION METHOD OF DISPLAY DEVICE AND DEFECT DETECTION APPARATUS OF DISPLAY DEVICE

CROSS-REFERENCE TO RELATED APPLICATION

This is a Continuation Application of International Patent Application No. PCT/JP2008/002687, filed on Sep. 26, 2008, which claims priority to Japanese Patent Application No. 2007-261481, filed on Oct. 5, 2007, and claims priority to and the benefit of U.S. Provisional Application No. 61/282,229, filed on Jan. 5, 2010. The contents of the aforementioned applications are incorporated herein by reference.

TECHNICAL FIELD

The present invention relates to flat panel display devices such as organic electroluminescence (EL) elements, liquid crystal display elements, or Field Emission Display (FED). Particularly, the present invention relates to a defect detection method and a defect detection apparatus of such display devices.

BACKGROUND

Display devices such as liquid crystal display elements have features that include compact size (small size), slimness (small thickness), low power consumption and lightness (light weight). Because of this, currently, the display devices are extensively used for various electronic equipments. Drive circuits or thin film transistors for driving these display devices have been manufactured using an exposure apparatus generally referred to as a stepper.

However, the size of liquid crystal display elements, in particular, is becoming ever larger, and after the $8^{th}$ generation, there occur many difficult problems, such as manufacturing costs and device transporting limitations, which cannot be solved by the scale-up extension of conventional technology. Further, in order to reduce the manufacturing costs, in addition to improving efficiency by increasing the substrate size, reduction in apparatus costs, reduction in running costs and improvement of a yield of a large-sized panel have become key points.

In addition, organic ELs, field emission displays and the like have been launched in the market, and reduction in an apparatus cost and reduction in a running cost have also become significant problems to be solved in relation to the manufacturing of next generation of those display devices.

Patent Document 1 discloses a method for manufacturing liquid crystal display elements using a flexible substrate which is in a roll shape as a countermeasure for the reduction of an apparatus cost of the liquid crystal display elements and the reduction of a running cost.

Patent Document 2 discloses a display defect detection method for detecting defects by selecting a resolution from an image of a liquid crystal panel, which is photographed with high accuracy by using a line sensor, according to the type of various display defects such as rubbing unevenness (ununiformity) or gap unevenness (ununiformity).

[Patent Citation 1] Japanese Patent No. 3698749
[Patent Citation 2] Japanese Patent Publication No. 2004-279239

The roll shaped flexible substrate has a length between several tens of meters and several hundreds of meters, as disclosed in the examples of Patent document 1. Therefore, it is necessary to stop a manufacturing line when a fatal defect is generated. Meanwhile, there also exist defective portions which can be simply repaired.

Patent Document 2 selects an image resolution according to the type of display defects in finished products (end-products) of liquid crystal display elements, but its purpose is only to find defects. Thus, whether or not the defects must be repaired is not determined.

SUMMARY

In light of such circumstances, the present invention provides a display device defect detection method and a display device defect detection apparatus, which can find a defective portion in a wiring and the like of a display device during a manufacturing process, and which can determine whether the defect can be repaired in a repair line or the defect requires a manufacturing line to be stopped.

A defect detection method of a display device which includes a plurality of pixels according to a first aspect, the defect detection method comprises a measurement process that measuring a feature amount for each partial region of the display device; a first determination process that determining whether the measured feature amount of each partial region is within a first range; a calculating process that calculating a difference between the feature amount of the partial region and a feature amount of a peripheral partial region of the partial region, with respect to a region which is determined as being within the first range in the first determination process; and a second determination process that determining whether the difference calculated by the calculating process is within a second range.

According to the defect detection method, even if the feature amount of the partial region is within the first range, if the difference between the partial region and the peripheral partial region thereof is large, the human eye seeing the display device recognizes the difference as luminance unevenness (ununiformity). The difference between the feature amount of the partial region and the feature amount of the peripheral partial region of the partial region is calculated to detect defects which cause the luminance unevenness (ununiformity).

A defect detection method of a display device according to a second aspect comprises a defect counting process that measuring a feature amount for each partial region of the display device, and counting a region which is determined as a defective region based on the measured feature amount of a region; a process that stopping a manufacturing line of the display device when a number of defects obtained in the defect counting process is greater than a first threshold value; a defect density calculating process that calculating a defect density in a predetermined area when the number of defects obtained in the defect counting process is smaller than the first threshold value; and a process that stopping the manufacturing line of the display device when the defect density obtained in the defect density calculating process is greater than a second threshold value.

In the defect detection method of the display device according to the second aspect, the defect density of the display device is calculated to determine whether to stop the manufacturing line. If the defect density is high, the defective regions are concentrated in one portion. In such a case, since simply repairing the portion is not sufficient, the defect density is employed as a determination reference.

A defect detection apparatus of a display device according to a third aspect comprises a feature amount determining section that measures a feature amount for each partial region of display device, and determines whether the measured feature amount of a region is within a first range; and a difference determining section that calculates a difference between the feature amount of the partial region and a feature amount of a peripheral partial region of the partial region, with respect to the partial region which is determined as being within the first range at the feature amount determining section, and determines whether the difference is within a second range.

Even if the feature amounts of the partial region is within the first range, if the difference between the partial region and the peripheral partial region thereof is large, the human eye seeing the display device recognizes the difference as luminance unevenness (ununiformity). In this regard, in the defect detection apparatus of the display device, the difference between the feature amount of the partial region and the feature amount of the peripheral partial region of the partial region is calculated to detect defects which cause the luminance unevenness (ununiformity).

A defect detection apparatus of a display device according to a fourth aspect comprises a defect number determining section that measures a feature amount for each partial region of the display device, and counts a number of defects in a partial region which is determined as a defective region based on the measured feature amount of the partial region, and determines whether the number of defects is greater than a first threshold value; and a defect density determining section that calculates the number of defects existing in a predetermined area when the defect number determining section determines that the number of defects is smaller than the first threshold value, and determines whether the number of defects existing in the predetermined area is greater than a second threshold value.

The fact that the number of defects existing in the predetermined area is greater than the second threshold value means that the defective regions are concentrated in one portion. In such a case, even if the defective regions are repaired, the repaired regions are visible. In this regard, the defect detection apparatus of the display device according to the fourth aspect detects the defect density.

A defect detection apparatus of a display device according to a fifth aspect comprises a defect density determining section that measures a feature amount for each partial region of the display device, counts a number of defects in the partial region which is determined as a defective region based on the measure feature amount of the partial region, calculates the number of defects existing in a predetermined area, and determines whether the number of defects existing in the predetermined area is greater than a second threshold value.

The defect detection apparatus of the display device according to the fifth aspect is possible to detect a defect of the display device by detecting the defect density.

A method for manufacturing a display device according to a sixth aspect comprises an element formation process that forming a pattern for a plurality of pixel region respectively; a measurement process that measuring a state of the pattern formed on a partial region, when a plurality of the partial region is divided in the display region including at least one of the pixel region; a first determination process that obtaining a first determination information which indicates a first state or a second state, in which the measured pattern state is within a predetermined reference in the first state, and the measured pattern state out of the reference range in the second state; a second determination process that obtaining a second determination information, in which comparing the first determination information of at least two partial regions which are adjacent to each other among the plurality of the partial regions, when all the compared first determination information indicate the second state, the second determination information indicates a display unevenness (ununiformity).

The defect detection method and defect detection apparatus of the display device according to the present invention, a defective portion in a wiring and the like of the display device can be found during a manufacturing process, and whether the defect can be repaired in a repair line or the defect requires a manufacturing line to be stopped can be determined.

BRIEF DESCRIPTION OF THE DRAWINGS

FIG. 2A to FIG. 2C are schematic views showing monitoring of a first mark AM and a second mark BM of a diffraction grating in an electrode formation process of a manufacturing apparatus 100 for an organic EL element.

FIG. 3A to FIG. 3C are views showing the states of a bottom-contact type organic EL element in which a light emitting layer IR and an ITO electrode are formed.

FIG. 4A to FIG. 4C are views illustrating a first monitoring apparatus CH1 in a partition wall formation process.

DESCRIPTION OF EMBODIMENTS

An apparatus for manufacturing a display device (display element) described in the present embodiment can be applied to an organic EL element, a liquid crystal display element or a field emission display. An apparatus and a method for manufacturing the organic EL element will be representatively described.

<<Apparatus for Manufacturing Organic EL Element>>

In the case of manufacturing the organic EL element, it is necessary to form a substrate on which a thin film transistor (TFT) and a pixel electrode are formed. In order to accurately form one or more organic compound layers (light emitting element layers), which include a light emitting layer on the pixel electrode which is formed on the substrate, it is necessary to form partition walls BA (bank layer) simply and accurately on a boundary region of the pixel electrode.

Figure 1:
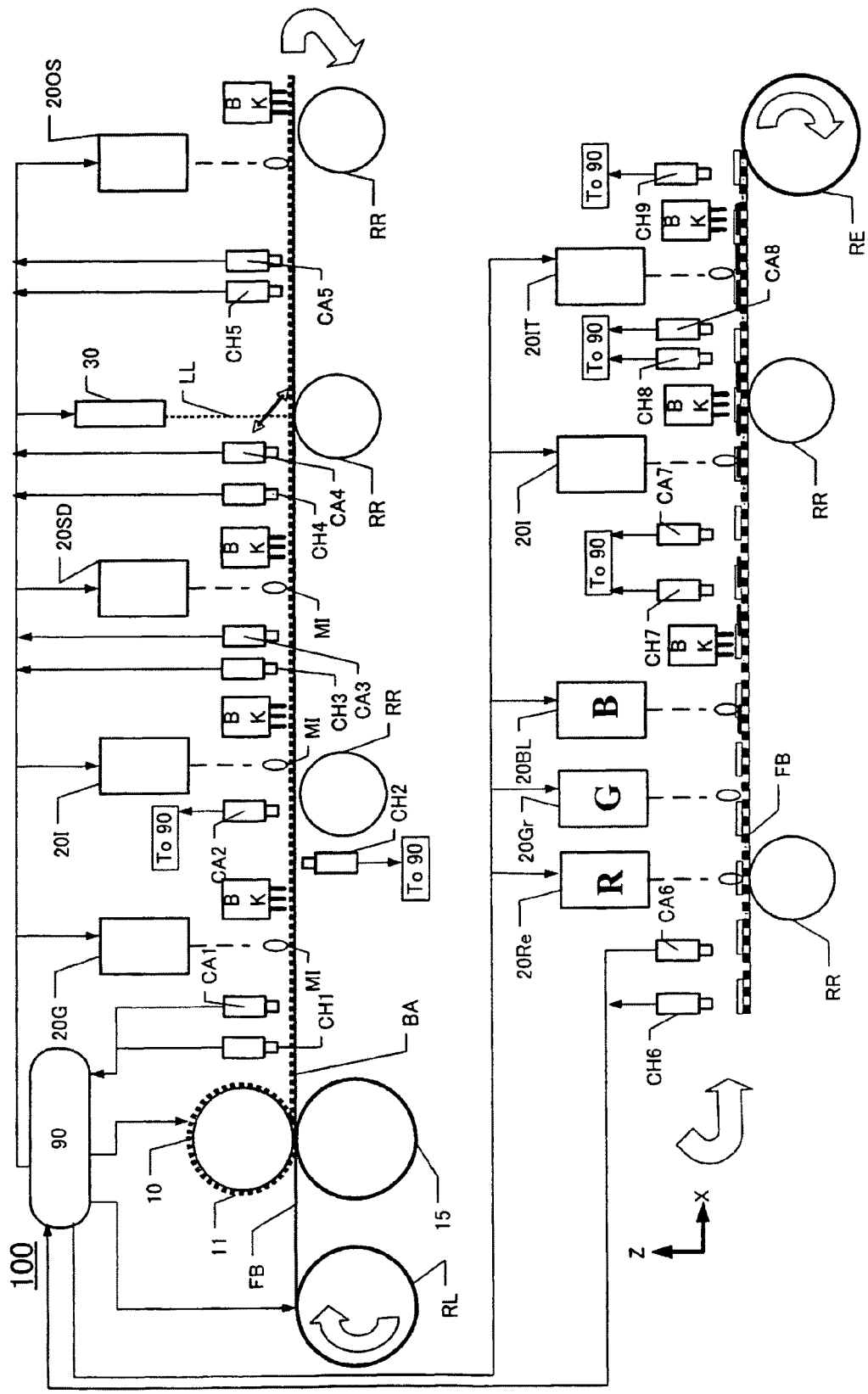
FIG. 1 is a schematic view showing the configuration of a manufacturing apparatus 100 for manufacturing an organic EL element on a flexible substrate FB.

FIG. 1 is a schematic view showing the configuration of a manufacturing apparatus 100 which manufactures an organic EL element 50 which includes a pixel electrode and a light emitting layer on a flexible substrate.

The manufacturing apparatus 100 for an organic EL element includes a supply roll (feeding roll) RL for supplying a band-shaped flexible sheet substrate FB which is wound in a roll shape. For example, the sheet substrate FB may have a length of 200 meters or more. The supply roll RL is rotated at a predetermined speed, so that the sheet substrate FB is fed in an X-axial direction (longitudinal direction) which is a transporting direction. Further, the manufacturing apparatus 100 for the organic EL element includes rollers RR at a plurality of positions, and rotating of these rollers RR, the sheet substrate FB is fed in the X-axial direction. The rollers RR may be rubber rollers which grip the sheet substrate FB from both surfaces thereof, or, if the sheet substrate FB has perforations, then the rollers RR may be ratchet rollers.

The manufacturing apparatus 100 for the organic EL element includes a wind-up roll RE for winding the sheet substrate FB into a roll shape in the final process thereof. Further, for a processing in a repair process of a defective portion, the wind-up roll RE winds the sheet substrate FB at a predetermined speed which is synchronized with that of the supply roll RL and the rollers RR.

<Partition Wall Formation Process>

The sheet substrate FB which has been fed from the supply roll RL is initially subject to a partition wall formation process in which the partition walls BA are formed on the sheet substrate FB. In the partition wall formation process, the sheet substrate FB is pressed by an imprint roller 10, and the sheet substrate FB is heated by a thermal transfer roller 15 to a glass transition point or higher, such that the shape of the pressed partition walls BA is maintained. Therefore, a pattern formed on the roller surface of the imprint roller 10 is transferred to the sheet substrate FB.

The roller surface of the imprint roller 10 is mirror-finished, and a fine imprint mold 11 which is made from a material such as SiC, Ta and the like is mounted on this roller surface. The fine imprint mold 11 has a stamp for a wiring of a thin film transistor and a stamp for a display pixel. Further, in order to form a first mark AM and a second mark BM (refer to FIG. 2) at both sides in the width direction of the band-shape flexible substrate FB, the fine imprint mold 11 also has stamps for the first mark AM and the second mark BM.

The first mark AM and the second mark BM are formed simultaneously with the formation of the partition walls BA for the wiring of the thin film transistor and the display pixel. Therefore, the positional accuracy between the partition wall BA and the first and second marks AM and BM is equal to the positional accuracy of the fine imprint mold 11.

A first monitoring apparatus CH1 is provided downstream in the X-axis direction from the imprint roller 10. The first monitoring apparatus CH1 monitors (observes) whether or not the partition walls BA for the wiring of the thin film transistor and the display pixel have been accurately formed. The first monitoring apparatus CH1 includes a camera which is composed of a one-dimensional CCD or a two-dimensional CCD, a laser length measuring device and the like. First alignment sensors CA1 are provided downstream of the first monitoring apparatus CH1.

<Electrode Formation Process>

After the first mark AM and the second mark BM are detected by the first alignment sensors CA1, the sheet substrate FB continues to move in the X-axis direction and is subject to an electrode formation process.

A thin film transistor (TFT) may employ either an inorganic semiconductor based or an organic semiconductor. If the thin film transistor is formed using the organic semiconductor, the thin film transistor can be formed by utilizing a printing technology and/or a droplet applying technology.

Among thin-film transistors which use organic semiconductors, a field effect transistor (FET) is particularly preferred. The electrode formation process shown in FIG. 1 will be described with an FET bottom gate type organic EL element 50. After a gate electrode G, a gate insulating layer I, a source electrode S, a drain electrode D and a pixel electrode P are formed on the sheet substrate FB, an organic semiconductor layer OS is formed.

In the electrode formation process, a droplet applying apparatus 20 is used which receives position information from the first alignment sensors CA1 and applies (coats) droplets onto the sheet substrate FB. The droplet applying apparatus 20 can employ an inkjet method or a dispenser method. The inkjet method includes a charge control method, a press vibration method, an electrical mechanical conversion method, an electrical heat exchange method, an electrostatic suction method and the like. According to a droplet applying method, material can be used less wastefully and a predetermined amount of material can be accurately applied in a predetermined position. Hereinafter, a droplet applying apparatus 20 for a gate electrode G will be distinguished as a gate droplet applying apparatus 20G in which G is added to the end thereof. The same applies for the other droplet applying apparatuses 20. In addition, the amount of one droplet of metal ink MI applied by the droplet applying method is between, for example, 1 and 300 nanograms.

The gate droplet applying apparatus 20G applies the metal ink MI inside the partition walls BA of a gate bus line GBL. Then, the metal ink MI is dried or baked using warm air or radiant heat such as far-infrared rays in a heat treatment apparatus BK. In this way, the gate electrode G is formed. The metal ink MI is a liquid in which conductive bodies having a particle diameter of approximately 5 nm is stably dispersed in a solvent at room temperature, and carbon, silver (Ag), gold (Au) or the like are used as the conductive bodies.

A second monitoring apparatus CH2 is provided downstream of the gate droplet applying apparatus 20G. The second monitoring apparatus CH2 monitors whether the metal ink MI has been applied on the gate bus line GBL and serves as a conductive line. The second monitoring apparatus CH2 includes a camera which is composed of a one-dimensional CCD or a two-dimensional CCD. A second alignment sensor CA2 is provided downstream of the second monitoring apparatus CH2.

Next, an insulating layer droplet applying apparatus 20I receives position information from the second alignment sensor CA2 and applies electrical insulating ink of polyimide-based resin or urethane-based resin on a switching portion. Then, the electrical insulating ink is dried and cured by warm air or radiant heat such as far-infrared rays by a heat treatment apparatus BK. In this way, the gate insulating layer I is formed.

A third monitoring apparatus CH3 is provided downstream of the insulating layer droplet applying apparatus 20I. The third monitoring apparatus CH3 monitors whether the electrical insulating ink is applied on an accurate position. The third monitoring apparatus CH3 also includes a camera which is composed of a one-dimensional CCD or a two-dimensional CCD. A third alignment sensor CA3 is provided downstream of the third monitoring apparatus CH3.

Next, a droplet applying apparatus 20SD for source, drain and pixel electrode (source, drain, and pixel electrodes droplet applying apparatus 20SD) receives position information from the third alignment sensor CA3 and applies the metal ink MI inside the partition walls BA of a source bus line SBL and inside the partition walls BA of the pixel electrode P. Then, the metal ink MI is dried and baked by a heat treatment apparatus BK. In this way, an electrode in which the source electrode S, the drain electrode D, and the pixel electrode P are connected to each other is formed.

A fourth monitoring apparatus CH4 is provided downstream of the droplet applying apparatus 20SD for source, drain, and pixel electrodes. The fourth monitoring apparatus CH4 monitors whether the metal ink MI has been applied on an accurate (correct) position. The fourth monitoring apparatus CH4 also includes a camera which is composed of a one-dimensional CCD or a two-dimensional CCD. A fourth alignment sensor CA4 is provided downstream of the fourth monitoring apparatus CH4.

Next, a cutting apparatus 30 receives position information from the fourth alignment sensor CA4 and cuts the source electrode S and the drain electrode D which are connected to each other. It is preferred to use a Femtosecond laser as the cutting apparatus 30. An irradiation portion of the Femtosecond laser which uses a titanium sapphire laser irradiates laser light LL with a wavelength of 760 nm in pulses of 10 KHz to 40 KHz while oscillating the laser light LL to the left and right and up and down.

The cutting apparatus 30 can perform processing of a submicron order by using the Femtosecond laser, and can accurately cuts a gap between the source electrode S and the drain electrode D, which decides the properties of the field effect transistor. The gap between the source electrode S and the drain electrode D is approximately 20 μm to 30 μm. Through the cutting process, an electrode in which the source electrode S is separated from the drain electrode D is formed. In addition to the Femtosecond laser, it is possible to use a carbon gas laser, a green laser or the like. Further, in addition to the laser, the gap may be mechanically cut by a dicing saw or the like.

A fifth monitoring apparatus CH5 is provided downstream of the cutting apparatus 30. The fifth monitoring apparatus CH5 monitors whether the gap between the source electrode S and the drain electrode D has been accurately formed. The fifth monitoring apparatus CH5 also includes a camera which is composed of a one-dimensional CCD or a two-dimensional CCD. A fifth alignment sensor CA5 is provided downstream of the fifth monitoring apparatus CH5.

Next, an organic semiconductor droplet applying apparatus 20OS receives position information from the fifth alignment sensor CA5 and applies organic semiconductor ink on a switching portion between the source electrode S and the drain electrode D. Then, the organic semiconductor ink is dried and baked by warm air or radiant heat such as far-infrared rays by a heat treatment apparatus BK. In this way, the organic semiconductor layer OS is formed.

In addition, a compound used to form the organic semiconductor ink may be single crystalline material or amorphous material, and may be either a low molecular compound or a high molecular compound. Particularly preferable examples include single crystal or π-conjugated polymer of a condensed ring aromatic hydrocarbon compound, which is representatively referred to as pentacene, triphenylene, anthracene or the like.

A sixth monitoring apparatus CH6 is provided downstream of the organic semiconductor droplet applying apparatus 20OS. The sixth monitoring apparatus CH6 monitors whether the organic semiconductor ink has been applied on an accurate position. The sixth monitoring apparatus CH6 also includes a camera which is composed of a one-dimensional CCD or a two-dimensional CCD. A sixth alignment sensor CA6 is provided downstream of the sixth monitoring apparatus CH6.

<Light Emitting Layer Formation Process>

The manufacturing apparatus 100 for the organic EL element continuously performs a process to form a light emitting layer IR of the organic EL element on the pixel electrode P.

In the light emitting layer formation process, the droplet applying apparatus 20 is used. As described above, it is possible to employ the inkjet method or the dispenser method. Further, according to the present embodiment, the light emitting layer can also be formed using a print roller (which will not be described in detail).

The light emitting layer IR contains a host compound and a phosphorescent compound (also referred to as a phosphorescent light emitting compound). The host compound is contained in a light emitting layer. The phosphorescent compound allows light emitted from the excited triplet can be observed and emits phosphorescent light at room temperature.

A droplet applying apparatus 20Re for a red light emitting layer receives position information from the sixth alignment sensor CA6 and applies R solution onto the pixel electrode P so as to form a film whose thickness after drying is approximately 100 nm. The R solution is obtained by dissolving a polyvinylcarbazole (PVK) host material and red dopant in 1,2-dichloroethane.

Then, a droplet applying apparatus 20Gr for a green light emitting layer receives position information from the sixth alignment sensor CA6 and applies G solution onto the pixel electrode P. The G solution is obtained by dissolving the PVK host material and green dopant in 1,2-dichloroethane.

Moreover, a droplet applying apparatus 20BL for a blue light emitting layer receives position information from the sixth alignment sensor CA6 and applies B solution onto the pixel electrode P. The B solution is obtained by dissolving the PVK host material and blue dopant in 1,2-dichloroethane.

Thereafter, the light emitting solution is dried and cured using warm air or radiant heat such as far-infrared rays by a heat treatment apparatus BK.

A seventh monitoring apparatus CH7 is provided downstream of the light emitting layer formation process. The seventh monitoring apparatus CH7 monitors whether the light emitting layers have been appropriately formed. A seventh alignment sensor CA7 is provided downstream of the seventh monitoring apparatus CH7.

Next, an insulating layer droplet applying apparatus 20I receives position information from the seventh alignment sensor CA7 and applies electrical insulating ink of polyimide-based resin or urethane-based resin on a part of the gate bus line GBL or the source bus line SBL such that there is no short-circuiting between these and a transparent electrode ITO which will be described later. Further, the electrical insulating ink is dried and cured using warm air or radiant heat such as far-infrared rays by a heat treatment apparatus BK.

An eighth monitoring apparatus CH8 is provided downstream of the insulating layer droplet applying apparatus 20I. The eighth monitoring apparatus CH8 monitors whether the electrical insulating ink has been applied. An eighth alignment sensor CA8 is provided downstream of the eighth monitoring apparatus CH8.

Thereafter, an ITO electrode droplet applying apparatus 20IT receives position information from the eighth alignment sensor CA8 and applies ITO (Indium Tin Oxide) ink on the red, green and blue light emitting layers. The ITO ink is a compound obtained by adding several percent of tin oxide ($SnO_2$) to indium oxide ($In_2O_3$), and the electrode thereof is transparent. Further, amorphous material such as IDIXO ($In_2O_3$—ZnO) can also be used to form a transparent conductive film. Preferably, the transparent conductive film has a transmittance of 90% or more. Then, the ITO ink is dried and cured by warm air or radiant heat such as far-infrared rays by a heat treatment apparatus BK.

A ninth monitoring apparatus CH9 is provided downstream of the ITO electrode droplet applying apparatus 20IT. The ninth monitoring apparatus CH9 monitors whether the electrical insulating ink has been applied.

In addition, the organic EL element 50 may include a positive hole transporting layer and an electron transporting layer, and these layers may be formed using a printing technology and/or a droplet applying technology.

The manufacturing apparatus 100 for the organic EL element includes a main control unit 90. Signals monitored by the first to ninth monitoring apparatuses CH1 to CH9 and alignment signals in the first to eighth alignment sensors CA1 to CA8 are transmitted to the main control unit 90. Further, the main control unit 90 controls the speed of the supply roll RL and the rollers RR.

<Formation of Alignment Mark & Counter Mark>

The sheet substrate FB is expanded or contracted in the X-axis direction and the Y-axis direction by passing through the thermal transfer roller 15 and the heat treatment apparatuses BK. Because of this, in the manufacturing apparatus 100 for the organic EL element, the first alignment sensors CA1 are provided downstream of the thermal transfer roller 15, and the second to eighth alignment sensors CA2 to CA8 are provided after the heat treatment apparatuses BK, respectively. Further, when an imprint defect, applying defect and the like has occurred, in the case of identifying defective portions and removing or repairing them, it is necessarily required to specify the defective portions. In this regard, in the present embodiment, the first mark AM is also used as the counter mark for checking (verify) the position of the X-axis direction.

Hereinafter, the control of the electrode formation process performed in the manufacturing apparatus 100 for the organic EL element will be described with reference to FIG. 2A to FIG. 2C.

In FIG. 2A, the sheet substrate FB has at least one first mark AM at both sides of the sheet substrate FB, respectively, with respect to the partition walls BA for the wiring of the thin film transistor and the partition walls BA for the pixel which are lined up in the Y-axis direction which is the width direction of the sheet substrate FB. For example, one second mark BM, for example, for every 50 first marks AM is formed adjacent to the first marks AM. For example, since the sheet substrate FB has a long length of 200 meters, the second marks BM are provided in order to make it easy to confirm at a predetermined interval that in which row the partition walls BA for the wiring of the thin film transistor and the partition wall BAs for the pixel are located. A pair of the first alignment sensors CA1 detects the first marks AM and the second marks BM and transmits a detection result to the main control unit 90.

The fine imprint mold 11 defines the positional relationship between the first and second marks AM and BM and the gate and source bus lines GBL and SBL of the field effect transistor.

Thus, the main control unit 90 detects shift in the X-axis direction, shift in the Y-axis direction and θ rotation by detecting a pair of the first marks AM. Further, the first marks AM may also be provided at the center region of the sheet substrate FB as well as both sides thereof.

The first alignment sensors CA1 constantly (always) monitors the sheet substrate FB moved in the X-axis direction and transmits images of the first marks AM to the main control unit 90. The main control unit 90 has a position counter 95 therein, and the position counter 95 counts row number of the organic EL elements 50 which are lined up in the Y-axis direction among the organic EL elements 50 formed on the sheet substrate FB. Since the rotation of the rollers RR is controlled by the main control unit 90, it is possible to ascertain (understand) the row number of the organic EL element 50 which is reached the position of the gate droplet applying apparatus 20G or the row number of the organic EL element 50 which is reached the position of the second monitoring apparatus CH2.

The position counter 95 confirms (checks) whether an error exists when counting the row number by the first marks AM based on the image of the second mark BM transmitted from the first alignment sensors CA1. For example, it is possible to prevent that the row number cannot be accurately ascertained when there are defects in the locations of the first marks AM of the fine imprint mold 11.

The gate droplet applying apparatus 20G is disposed in the Y-axis direction, and in which a plurality of columns of nozzles 22 are arranged in the Y-axis direction, and a plurality of rows (multirow) of nozzles 22 are arranged in the X-axis direction. The gate droplet applying apparatus 20G switches the timing, at which the metal ink MI is applied from the nozzles 22, as well as the nozzles 22 applying the metal ink MI in accordance with a position signal from the main control unit 90 based on the first alignment sensors CA1.

The heat treatment apparatus BK is provided downstream of the gate droplet applying apparatus 20G and this heat treatment apparatus BK dries the metal ink MI applied by the gate droplet applying apparatus 20G. The second monitoring apparatus CH2 is provided downstream of the heat treatment apparatus BK.

The second monitoring apparatus CH2 transmits a monitored image signal to the main control unit 90, and the main control unit 90 identifies defective portions in the applying of the metal ink MI, by comparing a region, in which the metal ink MI must be applied by the gate droplet applying apparatus 20G with the monitored image signal. The position in the organic EL element 50 and the row number of the organic EL element 50 where a defective portion occurred, or how many millimeters was the defective portion from the first marks AM are identified in the Y-axial direction by image processing. The row number of the organic EL element 50 where a defective portion occurred in the X-axial direction is identified based on the position counter 95, and the position in the organic EL element 50 of that row is also identified.

The first mark AM and the second mark BM are composed of diffraction gratings GT. The first mark AM is a dot-shaped diffraction grating GT arranged in the X-axis direction and the Y-axis direction as illustrated in the upper part of FIG. 2B. The section of the dot-shaped diffraction gratings GT is illustrated in the lower part of FIG. 2B. In addition, although not shown in the drawing, the second mark BM also is a dot-shaped diffraction grating GT similarly to the first mark AM.

FIG. 2C shows an alignment sensor CA for detecting the first mark AM and the second mark BM. In order to detect the first mark AM and the second mark BM, coherent light such as He—Ne laser light ($\lambda=0.6328$ μm) is irradiated onto first mark AM and the second mark BM. Then, a±n order image (n=1, 2, . . . ) from the dot-shaped diffraction grating GT is detected via a lens LEN.

If an interval (i.e., a grating constant) of the dot-shaped diffraction grating GT is taken as L, a wavelength of the coherent light is taken as λ, and if an angle between the coherent light irradiation angle (irradiation direction) and alignment direction of the alignment sensor CA are taken as θ, then a relationship of L sin θ=nλ(n=±1, ±2, ...) is established.

As illustrated in the graph shown in FIG. 2C, the alignment sensor CA detects a waveform-shaped signal in the portion where the dot-shaped diffraction grating GT exists, but detects no signal in the portion where the dot-shaped diffraction grating GT does not exist. Because of this, the position counter 95 digitalizes the detected signal, and counts the row number of the organic EL element 50, which are arranged in the Y-axis direction, among the organic EL elements 50 formed on the sheet substrate FB. Thus, it is possible to accurately and quickly ascertain the position of the organic EL element 50. Further, since the first mark AM and the second mark BM are diffraction gratings GT, they are less contaminated.

<<Organic EL Element 50 Formed on Partition Wall of Field Effect Transistor>>

FIG. 3A to FIG. 3C are views showing the state of a bottom-contact type organic EL element in which the light emitting layer IR and ITO electrode are formed. In the organic EL element 50, the gate electrode G, the gate insulating layer I, the pixel electrode P, the organic semiconductor layer OS, the light emitting layer IR and the ITO electrode are formed on the sheet substrate FB.

In FIG. 3A to FIG. 3C, the sheet substrate FB is composed of a heat resistance resin film. In detail, polyethylene resin, polypropylene resin, polyester resin, ethylene-vinyl copolymer resin, polyvinyl chloride resin, cellulose resin, polyamide resin, polyimide resin, polycarbonate resin, polystylene resin, vinyl acetate and the like can be used for the sheet substrate FB.

As described above, since the sheet substrate FB is subject to the heat treatment of the heat transfer in the partition wall formation process and various types of ink must be dried or baked by the heat treatment apparatus BK, the sheet substrate FB is heated to approximately 200 degrees. Preferably, the sheet substrate FB has a small thermal expansion coefficient such that the dimensions thereof do not change when heat applied thereto. For example, the thermal expansion coefficient can be reduced by mixing inorganic filler with resin film. For example, the inorganic filler includes titanium oxide, zinc oxide, alumina, silicon oxide and the like.

As shown in FIGS. 3B and 3C, because the partition wall BA allows are present, the electrodes, the light emitting layer and the like can be formed accurately and uniformly. Since the sheet substrate FB is moved by the rollers RR in the X-axis direction (longitudinal direction) at a high speed, even if there is a possibility that the droplet applying apparatus 20 will not be able to accurately apply the droplets, the electrodes, the light emitting layer and the like can be formed accurately and uniformly.

In addition, the manufacturing apparatus 100 can be used for manufacturing various field effect transistors in addition to the field effect transistor illustrated in FIGS. 3A to 3C. For example, a top-gate type field effect transistor can also be manufactured by changing the sequence of ink applied on the sheet substrate FB.

<<Monitoring Apparatus CH>>

Hereinafter, various monitoring apparatuses CH will be described with reference to FIGS. 4A to 7B.

FIGS. 4A to 4C are a diagram illustrating the first monitoring apparatus CH1 in the partition wall formation process.

FIG. 4A is a top view of the sheet substrate FB imprinted by the fine imprint mold 11. Further, FIG. 4B is a sectional view taken along line c-c shown in FIG. 4A. FIG. 4C is a schematic view illustrating the state in which the first monitoring apparatus CH1 monitors the partition walls BA.

Since the partition walls BA of the sheet substrate FB, which are formed by the fine imprint mold 11, serve as a base of an wiring and the like, it is important whether the partition walls BA are accurately formed in the sequent applying process of the metal ink MI. As illustrated in FIG. 4B, the partition walls BA are originally to be formed as indicated by a solid line. However, dust may be attached to the fine imprint mold 11 or the sheet substrate FB, so a defective partition wall E-BA having an inaccurate (incorrect) shape may be formed. Therefore, a groove GR between the partition walls BA on which the metal ink MI is applied is not formed accurately.

For example, the first monitoring apparatus CH1 illustrated in FIG. 4C is a laser measuring instrument, and includes a laser source LED, a lens LEN and a sensor SEN. Further, the laser source LED irradiates light onto the sheet substrate FB, and reflected light thereof is received in the sensor SEN, so that the height of the partition walls BA is measured.

Figure 5C:
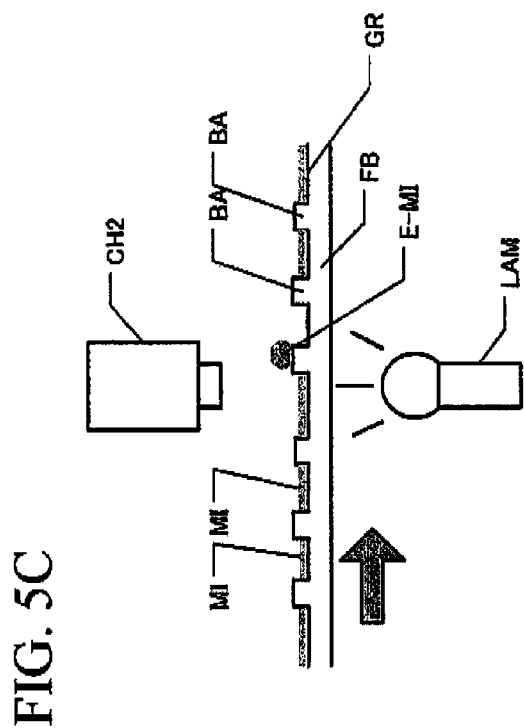
FIG. 5A to FIG. 5C are views illustrating a second monitoring apparatus CH2 in an electrode formation process.
Figure 5A:
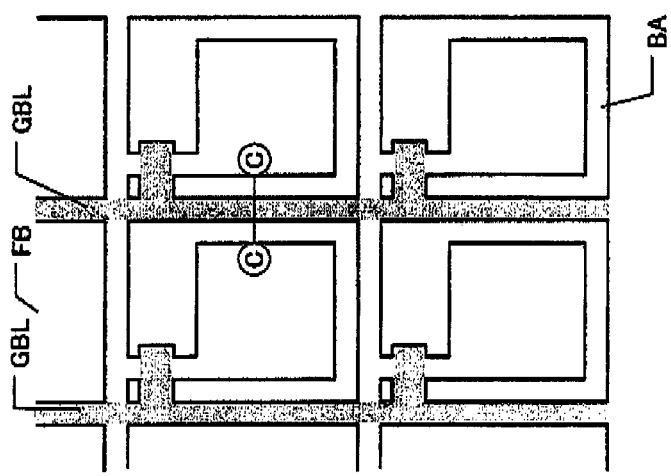
Figure 5B:
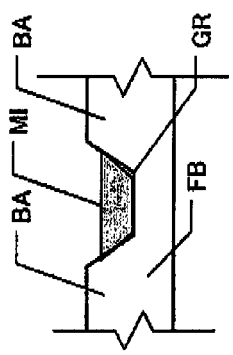

FIGS. 5A to 5C are views illustrating the second monitoring apparatus CH2 in the electrode formation process. FIG. 5A is a top view of the sheet substrate FB which is completed the electrode formation process. Further, FIG. 5B is a sectional view taken along line c-c shown in FIG. 5A. FIG. 5C is a schematic view illustrating the state in which the second monitoring apparatus CH2 monitors the gate bus line GBL.

Under normal circumstances, the metal ink MI is accurately applied in the groove GR between the partition walls BA for the gate bus line GBL as shown in FIG. 5A, and the metal ink MI is dried or baked by the heat treatment apparatus BK, so that the metal ink MI becomes a thin film as shown in FIG. 5B. However, due to malfunction of the nozzles 22 of the gate droplet applying apparatus 20G and the like, the metal ink MI may be applied on top of the partition wall BA or a portion which is different from a designed portion.

The second monitoring apparatus CH2 shown in FIG. 5C includes a one or two-dimensional camera. For example, the second monitoring apparatus CH2 illuminates the bottom surface of the sheet substrate FB from underneath by using a lamp LAM and monitors transmission light thereof. As illustrated in FIG. 5C, the state in which the metal ink MI has been applied on the partition wall BA can be monitored (observed). In addition, since many sheet substrate FB are transparent, placing the lamp LAM below the sheet substrate FB until the first-half process (i.e., the process in which monitoring is performed by the fourth monitoring apparatus CH4) makes monitoring easier than the case of monitoring a reflected light.

Figure 6B:
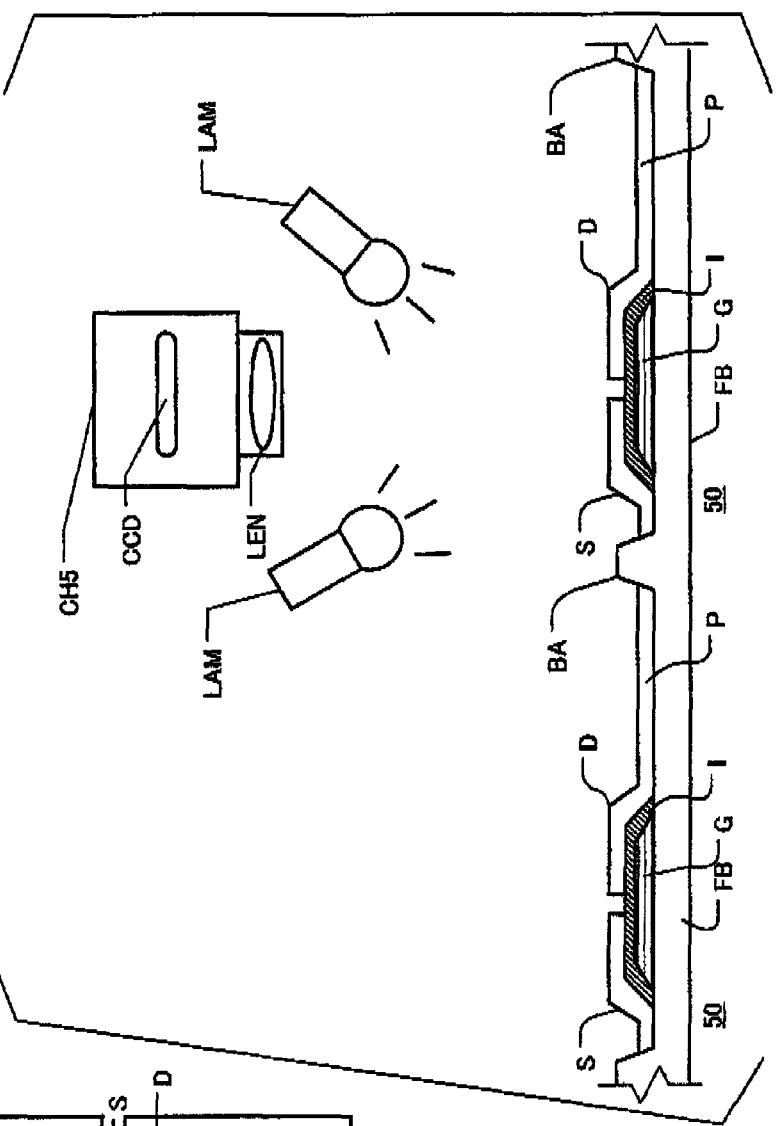
FIGS. 6A and 6B are views illustrating a fifth monitoring apparatus CH5 in a process of a cutting apparatus 30 for forming a gap between a source electrode S and a drain electrode D.
Figure 6A:
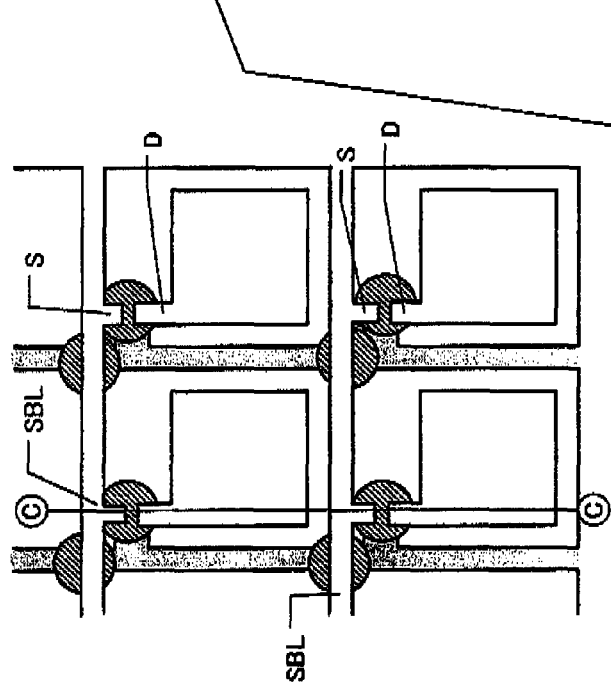

FIGS. 6A to 6B are views showing the fifth monitoring apparatus CH5 in the process of the cutting apparatus 30 for forming the gap between the source electrode S and the drain electrode D. FIG. 6A is a top view of the sheet substrate FB which is completed the cutting process. Further, FIG. 6B is a sectional view taken along line c-c shown in FIG. 6A and shows the state in which the fifth monitoring apparatus CH5 monitors the cutting state.

Since the gate electrode G and the gate insulating layer I have been already formed in the vicinity of the source electrode S and the drain electrode D, it is difficult for the fifth monitoring apparatus CH5 to monitor the gap between the source electrode S and the drain electrode D by using transmission light. In this regard, the lamp LAM is disposed in the vicinity of the fifth monitoring apparatus CH5 and the vicinity of the source electrode S and the drain electrode D is monitored.

<<Identification of Repair Portions>>

Figure 7A:
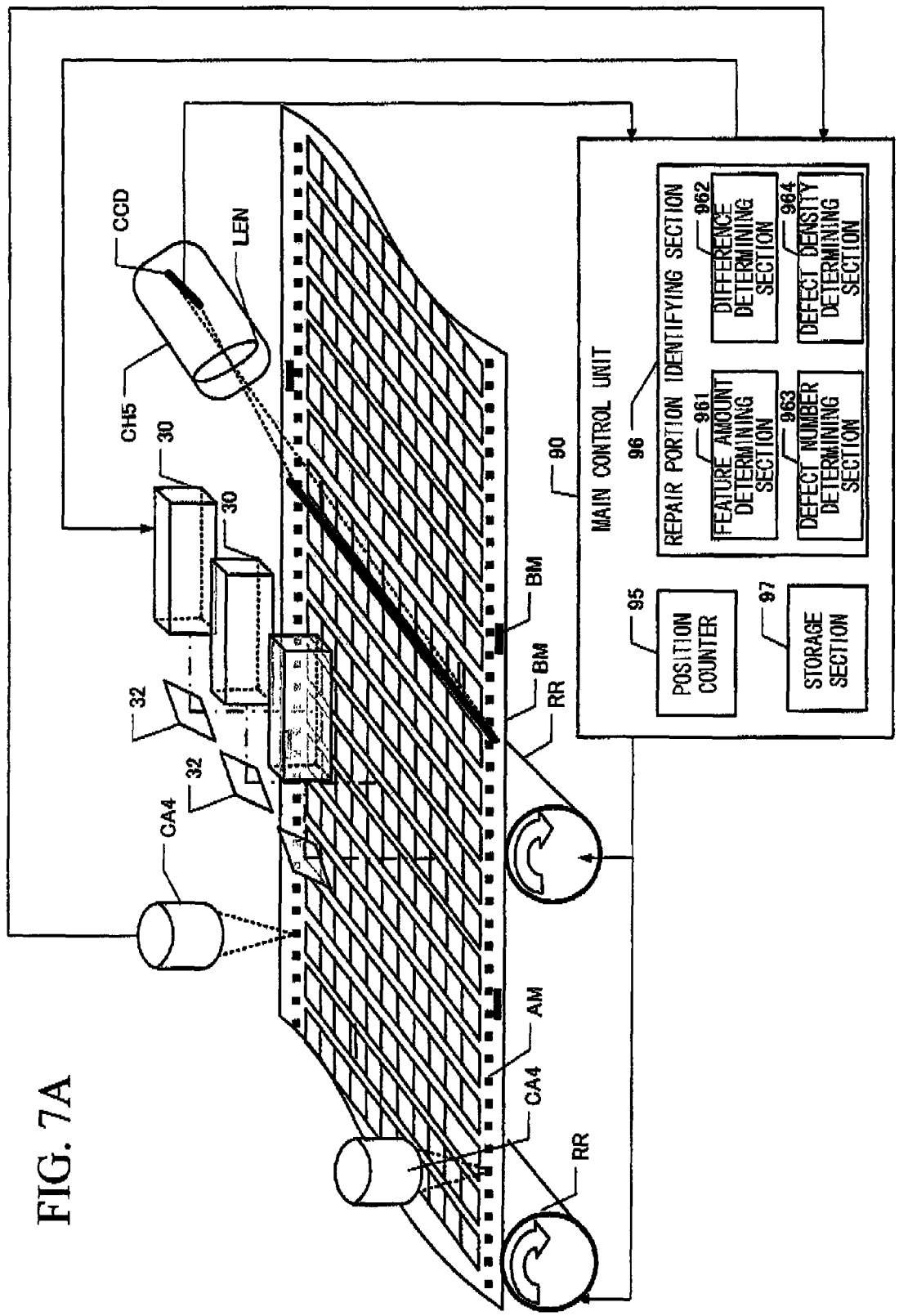
FIG. 7A is a perspective view from a fifth alignment sensor CA5 to a fifth monitoring apparatus CH5.

FIG. 7A is a perspective view from the fourth alignment sensor CA4 to the fifth monitoring apparatus CH5. Since the identification of repair portions (portions to be repaired) is basically performed in the same manner in other processes, monitoring of the gap between the source electrode S and the drain electrode D, which is formed by the cutting apparatus 30, will be described as a representative example.

The fourth alignment sensor CA4 is connected to the main control unit 90, and transmits the image signal of the first marks AM to the main control unit 90. The main control unit 90 measures the tilt and position in the Y-axis direction of the sheet substrate FB based on the image signal. Further, the main control unit 90 measures the stretching in the Y-axis direction of the sheet substrate FB by measuring the first marks AM at both sides of the sheet substrate FB.

The main control unit 90 also controls the rotation of the rollers RR, thus can also ascertain the movement speed in the X-axis direction of the sheet substrate FB, and outputs a signal to the cutting apparatus 30 such that the gap between the source electrode S and the drain electrode D of each organic EL element 50 is formed based on the first marks AM. After a laser is irradiated from the cutting apparatus 30, the direction of the laser is adjusted to a predetermined position by a Galvano mirror 32 and the like.

The main control unit 90 internally includes the position counter 95 that counts the position in the X-axis direction, a repair portion identifying section 96 that identifies defective portions, that is, repair portions which require repairing, and a storage section 97 that stores a design dimension of the organic EL element 50, the repair portions and the like. The repair portion identifying section 96 includes a feature amount determining section 961, a difference determining section 962, a defect number determining section 963 and a defect density determining section 964.

The fifth monitoring apparatus CH5 includes a lens LEN and a one-dimensional CCD therein. An image of the one-dimensional CCD is transmitted to the main control unit 90. The main control unit 90 can ascertain the state of the gap between the source electrode S and the drain electrode D, which is formed by the cutting apparatus 30. The repair portion identifying section 96 compares a design value stored in the storage section 97, that is, the gap between the source electrode S and the drain electrode D, with an actual gap between the source electrode S and the drain electrode D, which is formed by the cutting apparatus 30, thereby identifying a different portion as the defective portion. The repair portion identifying section 96 can identify the distance ($\mu$m) by which the defective portion is separated from the first mark AM in the X-axis direction and the Y-axis direction, and identify the row number of the organic EL element 50 based on the counting of the position counter 95. The identified repair portions are stored in the storage section 97 and data regarding the repair portions is used in the repair process.

Figure 7B:
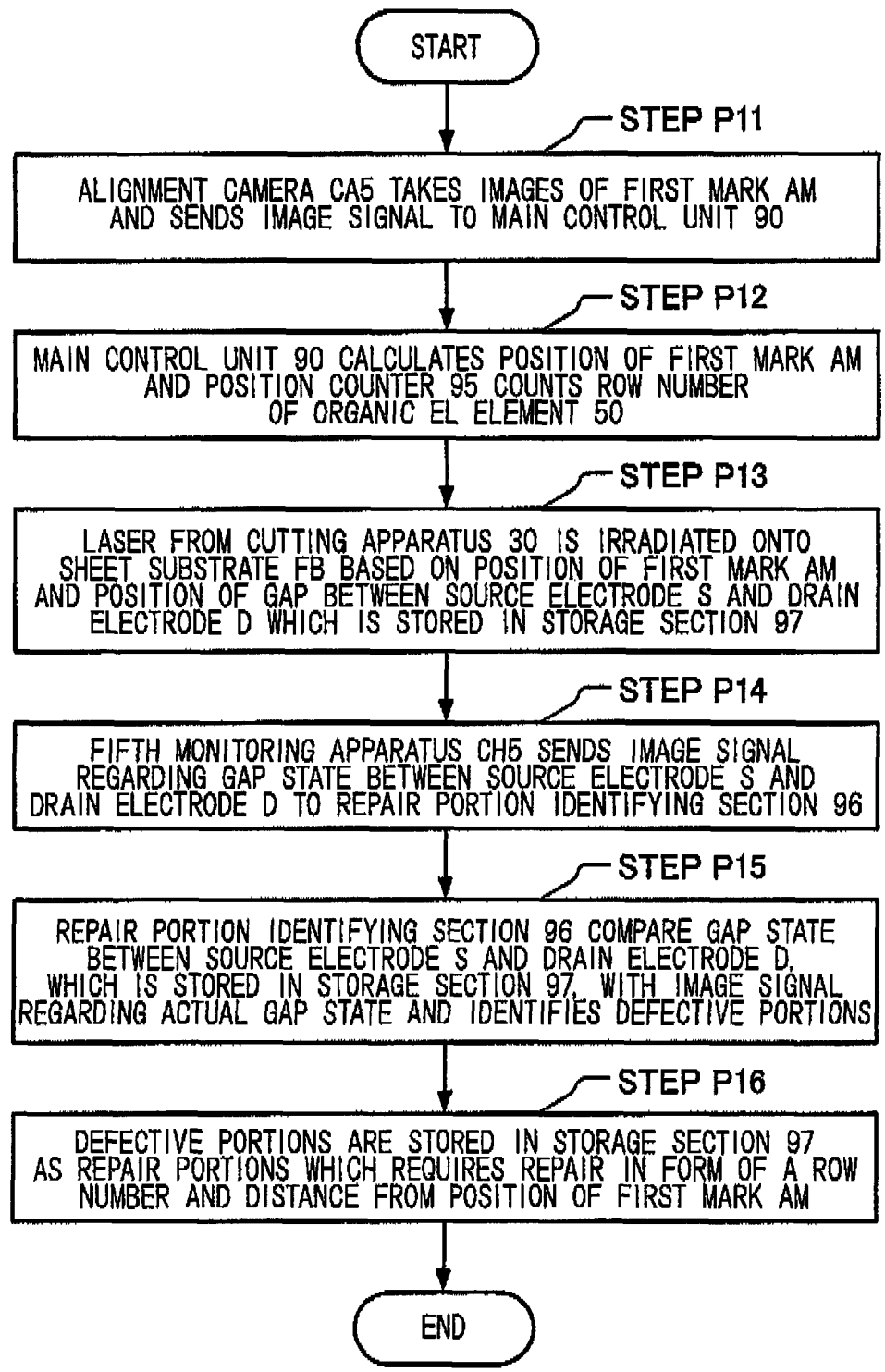
FIG. 7B is a flowchart illustrating a process of applying organic semiconductor ink and a process of storing repair portions shown in FIG. 7A.

FIG. 7B is a flowchart illustrating a process that forming the gap between the source electrode S and the drain electrode D shown in FIG. 7A and a process that storing the repair portions.

In Step P11, the alignment sensor CA5 takes images of the first mark AM, and sends an image signal to the main control unit 90.

In Step P12, the main control unit 90 calculates the position of the first mark AM, and the position counter 95 counts the row number of the organic EL element 50. The first mark AM is used for the cutting apparatus 30 to determine the position of the source electrode S and the drain electrode D, and is also used to identifying the row number of the organic EL element 50. In addition, the row number of the organic EL element 50 may also be identified by imaging the second mark BM using the fourth alignment sensor CA4 as described in FIG. 2A.

In Step P13, a laser is irradiated from the cutting apparatus 30 to the sheet substrate FB based on the position of the first mark AM and the position of the gap between the source electrode S and the drain electrode D which is stored in the storage section 97.

In Step P14, the fifth monitoring apparatus (observing apparatus) CH5 sends an image signal regarding the state of the gap between the source electrode S and the drain electrode D to the repair portion identifying section 96. Since the sheet substrate FB is moved in the X-axis direction, it is sufficient if the fifth monitoring apparatus CH5 is a one-dimensional CCD extending in the Y-axis direction. Since the movement speed of the sheet substrate FB is fast, if there is a lot of noises generated in the image signal regarding the gap between the source electrode S and the drain electrode D, then it is possible to prepare a two-dimensional CCD to which is connected a frame accumulation-type memory, which gradually shifts the accumulation location of the CCD to match the movement speed of the sheet substrate FB. This method is a kind of a CCD reading method which is generally referred to as TDI (Time Delayed Integration) method.

Next, in Step P15, the repair portion identifying section 96 compares the gap between the source electrode S and the drain electrode D, which is stored in the storage section 97, with the image signal regarding the actual gap state, thereby identifying the defective portion. The identifying of the defective portion will be described in detail with reference to FIGS. 8A, 8B and 8C.

In Step P16, the defective portions are stored in the storage section 97 as repair portions which requires repair, and is stored therein in form of the row number and the distance from the position of the first mark AM.

Figure 8A:
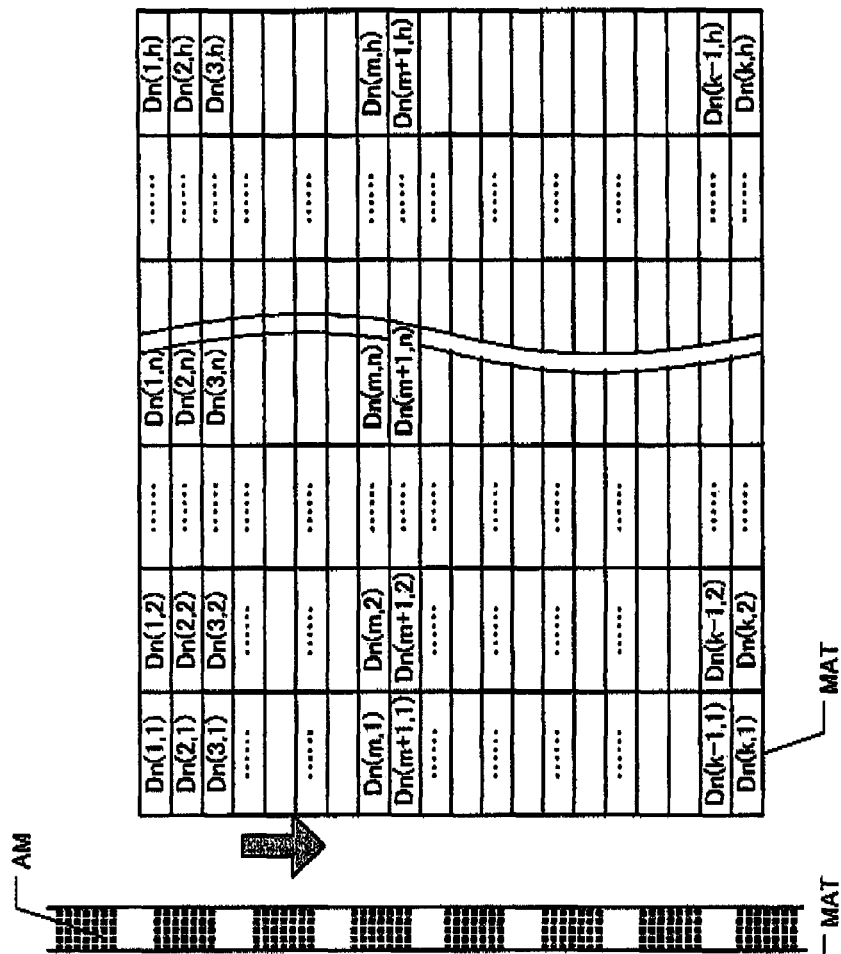
FIG. 8A is a view showing an organic EL element 50 monitored by a fifth monitoring apparatus CH5, a matrix MAT overlapped with the organic EL element 50, and data Dn (m, n) of the matrix MAT.

The left part (a) in FIG. 8A illustrates the organic EL elements 50 monitored by the fifth monitoring apparatus CH5 and a matrix MAT which is overlapped with the organic EL elements 50.

The one-dimensional CCD of the fifth monitoring apparatus CH5 can output image data for each pixel pitch in the Y-axis direction, and can also output image data in the X-axis direction of the sheet substrate FB at each predetermined pitch, by adjusting a sampling time, because the sheet substrate FB is moved in the X-axis direction at a constant speed. That is, it is possible to obtain an image data of subdivided partial regions with respect to the organic EL element 50. The image data is stored in the storage section 97 as the matrix MAT.

As illustrated in the left part (a) in FIG. 8A, since the first marks AM are formed on the sheet substrate FB, the image data of the subdivided partial regions is associated with position information in the X-axis direction and the Y-axis direction. In addition, the pixel pitch of the one-dimensional CCD, the magnification of the lens LEN and the like of the fifth monitoring apparatus CH5 illustrated in FIG. 7A are changed, so that the size of the subdivided partial regions can be changed.

The right part (b) in FIG. 8A is a view showing the subdivided partial regions stored in the storage section 97 as the matrix MAT. The subdivided partial regions are stored in the storage section 97 as data (Dn (m, n)) of the (k×h) matrix MAT (i.e. row k and column h in matrix MAT) together with position information of a region. However, it is not necessary to define the (k×h) matrix MAT according to the pixel pitch and the like of the one-dimensional CCD. Since the fifth monitoring apparatus CH5 has the main purpose of monitoring the gap between the source electrode S and the drain electrode D, one matrix may be provided for each pixel of the organic EL element 50, and the gap between the source electrode S and the drain electrode D may be stored in the storage section 97 together with the position information of the partial regions.

The repair portion identifying section 96 identifies the defective portions based on the data (Dn (m, n)) of the matrix MAT which is stored in the storage section 97. The identifying of the defective portion will be described in detail with reference to FIG. 8B.

Figure 8B:
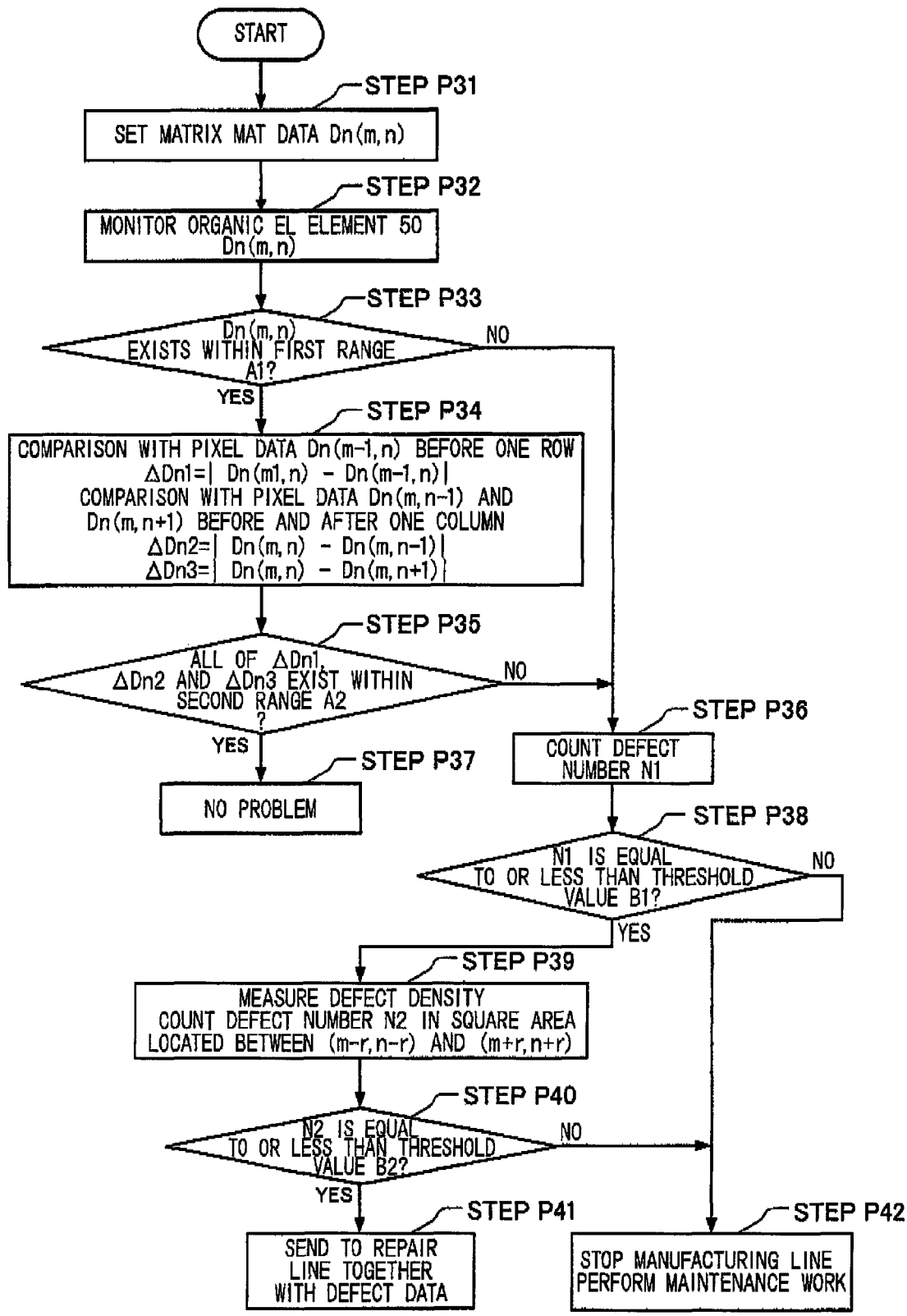
FIG. 8B is a defect determination flowchart illustrating a procedure of identifying a defective portion based on data Dn (m, n) of a matrix MAT.

FIG. 8B is a defect determination flowchart illustrating a procedure for identifying the defective portions based on the data Dn (m, n) of the matrix MAT, and determining a line stop of the manufacturing apparatus 100 shown in FIG. 1, a repair performed by a repair apparatus 110 to be described in FIG. 9, and the like.

In Step P31, the data Dn (m, n) of the (k×h) matrix MAT is set. The flowchart will be described on the assumption that data Dn (m, n) of one row and one column is allocated to one pixel (including one gate electrode G, one source electrode S, one drain electrode D and one pixel electrode P, respectively) of the organic EL element 50 for the purpose of convenience for the explanation.

In Step P32, the fifth monitoring apparatus CH5 monitors the organic EL element 50. By this, the data Dn (m, n) of the matrix MAT is transmitted to the repair portion identifying section 96. Since the fifth monitoring apparatus CH5 monitors the gap between the source electrode S and the drain electrode D, the gap corresponds to a feature amount monitored by the fifth monitoring apparatus CH5. For example, Dn (m, n) corresponds to dimension data when the gap is set to 25 µm, and then Dn (m, n)=25 µm is transmitted to the repair portion identifying section 96.

In Step P33, the feature amount determining section 961 (refer to FIG. 7A) of the repair portion identifying section 96 determines whether the gap data Dn (m, n) exists within a first range A1. For example, the first range A1 is 20 µm to 30 µm. In the determination of the feature amount determining section 961, if the data Dn (m, n) is 25 µm, Step P34 is performed. However, if the data Dn (m, n) is 15 µm or 35 µm, Step P36 is performed because the data Dn (m, n) is out of the first range A1.

In Step P34, the difference determining section 962 compares the data Dn (m, n) with data of a peripheral region of the data Dn (m, n). In detail, the difference determining section 962 calculates a difference between the data Dn (m, n) which is a feature amount and data Dn (m−1, n) of a pixel before one row (one row previous). That is, the difference determining section 962 calculates ΔDn1 which is equal to |Dn (m, n)−Dn (m−1, n)|. Further, the difference determining section 962 calculates differences between the data Dn (m, n) and data Dn (m, n−1) and Dn (m, n+1) of pixel before and after one column. That is, the difference determining section 962 calculates ΔDn2 which is equal to |Dn (m, n)−Dn (m, n−1)| and ΔDn3 which is equal to |Dn (m, n)−Dn (m, n+1)|.

In Step P35, the difference determining section 962 determines whether the differences ΔDn1, ΔDn2 and ΔDn3 exist within a second range A2. If all the differences ΔDn1, ΔDn2 and ΔDn3 exist within the second range A2, Step P37 is performed. However, if any one of the differences is out of the second range A2, Step P36 is performed. For example, the second range A2 is 0 to 5 µm.

In Steps P33 and P35, even if the feature amount determining section 961 determined that the Dn (m, n) exists in the first range A1, the difference determining section 962 further determines whether the differences ΔDn1, ΔDn2 and ΔDn3 exist in the second range A2, the reason for this is as follows. That is, the gap between the source electrode S and the drain electrode D in the organic EL element 50 exerts significant influence on light emission luminance. If the luminance difference between a pixel and other pixels around the pixel is large, since the human eye easily feels uncomfortable in regard to luminance unevenness (ununiformity) and the like, it is treated as a defective region. Meanwhile, if luminance is gradually changed, the human eye does not notice luminance unevenness (ununiformity). Even when data Dn (1, 1) and data Dn (k, h) exist in 21 µm and 29 µm respectively, if the change of luminance along the above range is small, the human eye does not recognize luminance unevenness (ununiformity).

In Step P36, the data Dn (m, n) is defined as defective regions and the number of the defective regions is counted.

In Step P37, it is determined that the pixel of the organic EL element 50 of the data Dn (m, n) is good product.

In Step P38, the defect number determining section 963 determines whether the defect number N1 (number of the defects) is equal to or less than a first threshold value B1. If the defect number N1 is greater than the first threshold value B1, since it is determined that the defect number N1 is too much and it cannot be handled at repair, and Step P42 is performed so that the line of the manufacturing apparatus 100 is stopped. Then, maintenance of the manufacturing apparatus 100 is performed. However, if the defect number N1 is equal to or less than the first threshold value B1, since it is determined that the defects can be basically handle by repair, because the defect number N1 is not large enough to stop the manufacturing apparatus 100, and Step P39 is performed.

In Step P39, the defect density determining section 964 calculates the defect number N2 in a square region located (interposed) between (m−r, n−r) and (m+r, n+r). In addition to the square region, a rectangular region may also be employed.

In Step P40, the defect density determining section 964 determines whether the defect number N2 in the square region is equal to or less than a second threshold value B2. If the defect number N2 in the square region is greater than the second threshold value B2, that is, a defect density is larger than the second threshold value B2, since it is determined that the defects are difficult to be handle at repair, because they are densely concentrated in one portion, and Step P42 is performed so that the line of the manufacturing apparatus 100 is stopped. Then, maintenance of the manufacturing apparatus 100 is performed. However, if the defect density is equal to or less than the second threshold value B2, Step P41 is performed so that the defects are repaired in a repair line.

Figure 9A:
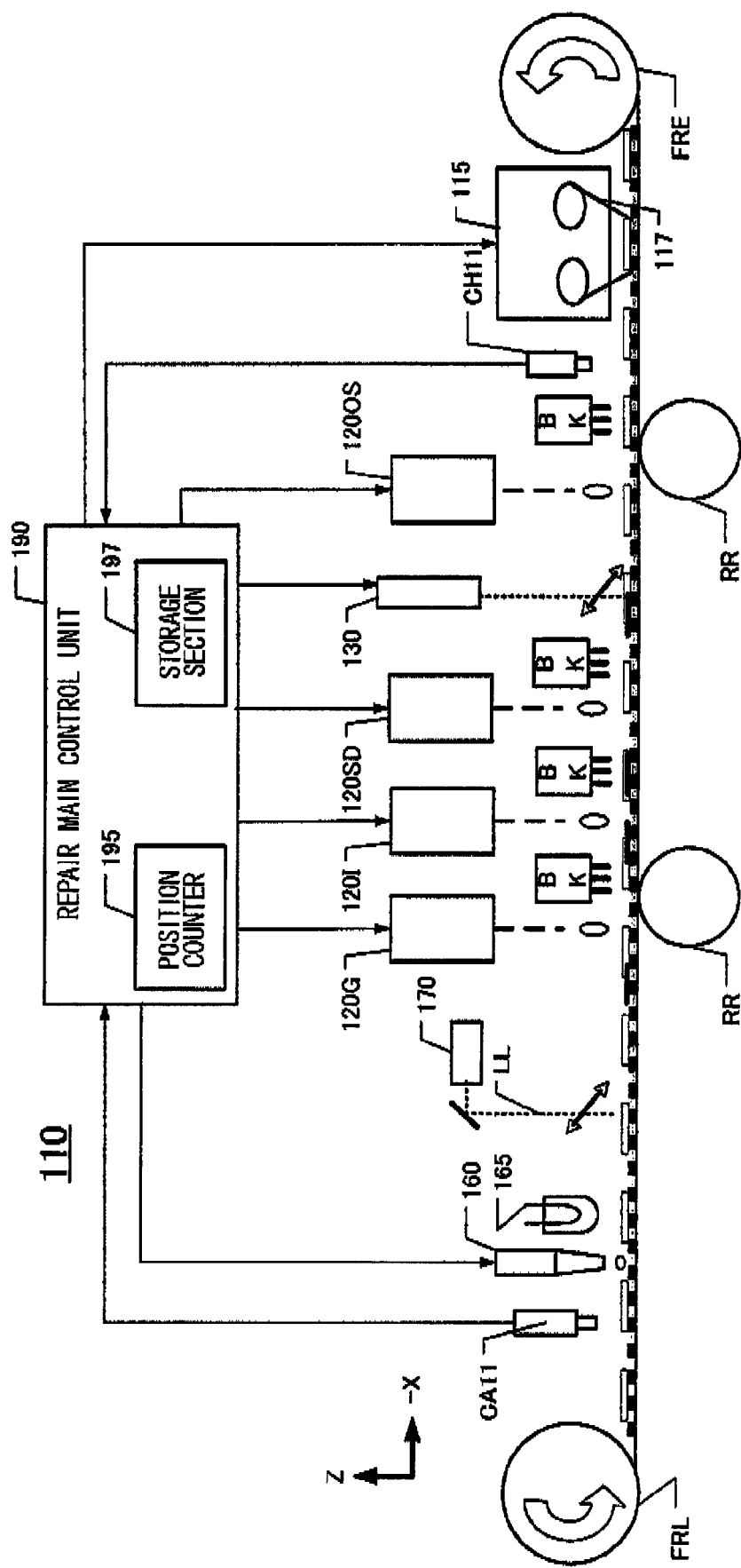
FIG. 9A is a schematic view showing a repair apparatus 110 that repairs an organic EL element 50 having repair portions through a batch processing.

In Step P41, the defective regions are repaired by the repair apparatus 110 and the like, which is to be described in FIG. 9A. The fact that the defect density is less than the second threshold value B2 means that the defective regions are scattered. Thus, even if the defective regions are repaired, the repaired regions are not visible. In addition, the data (Dn (m, n)) stored in the storage section 97 together with the position information is transmitted to a repair main control unit 190 of the repair apparatus 110.

In Step P42, after the line of the manufacturing apparatus 100 is stopped, maintenance work is performed such that no defects are generated.

Figure 8C:
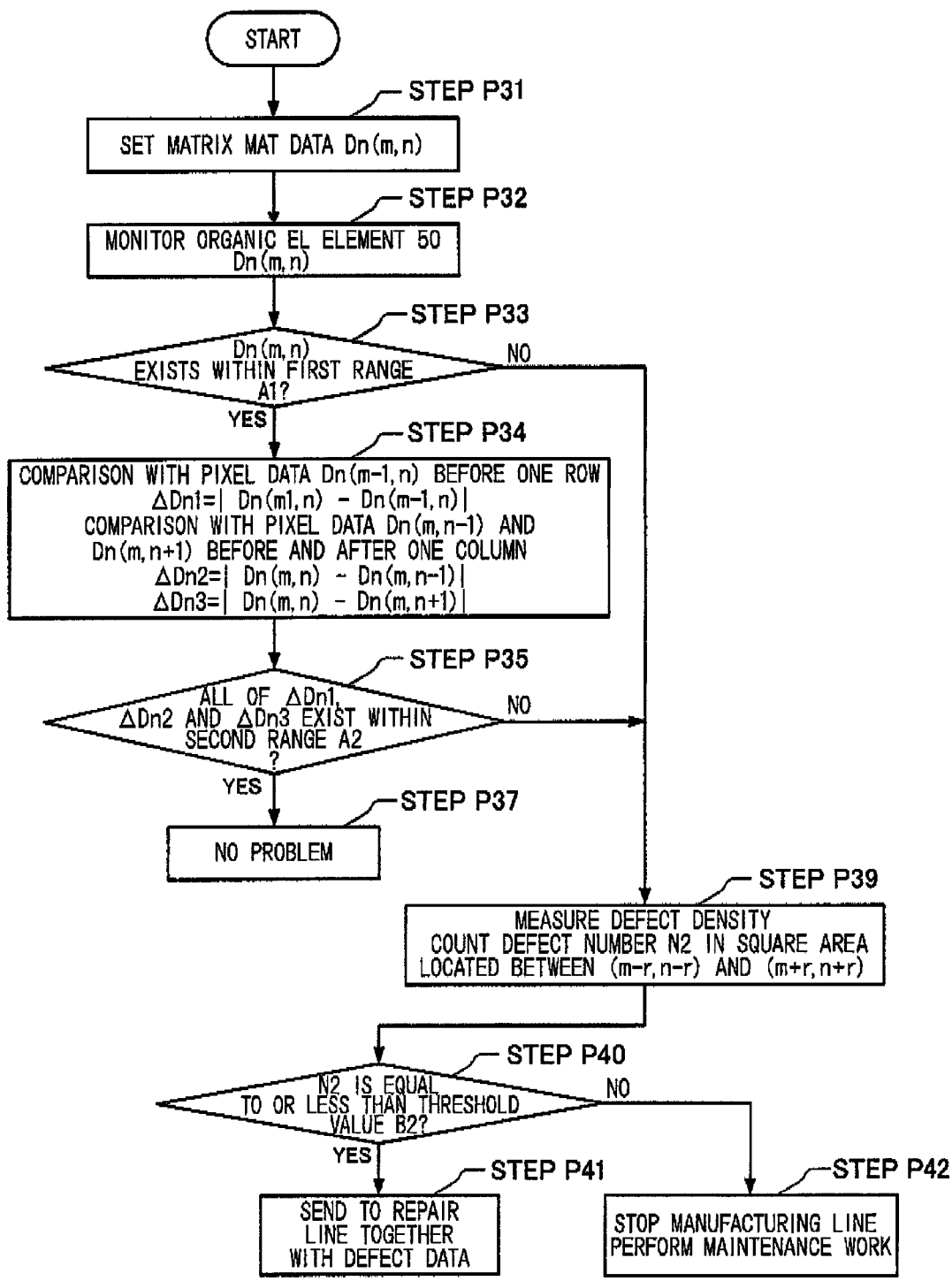
FIG. 8C is a flowchart different from a defect determination flowchart of FIG. 8B.

FIG. 8C is a flowchart different from the defect determination flowchart of FIG. 8B. In FIG. 8C, Steps P36 and P38 of FIG. 8 are omitted.

When the defect number N1 is large, even if the defect number determining section 963 does not exist, a case may often occur in which the defect density determining section 964 determines that the defect number N2 is larger than the second threshold value B2. Thus, even if Steps P36 and P38 are omitted, the same effects can be obtained.

In FIGS. 8A to 8C, the monitoring by the fifth monitoring apparatus CH5 of the gap between the source electrode S and the drain electrode D has been described. However, defect detection using the data Dn (m, n) of the matrix MAT can be likewise applied to the detection by the first monitoring apparatus CH1 of the height of the partition wall BA, the detection by the third monitoring apparatus CH3 of the applying position of the metal ink MI, and the like.

<<Repair Apparatus for Organic EL Element>>

FIG. 9A is a schematic view showing the repair apparatus 110 that repairs the organic EL element 50 having repair portions by a batch processing. The repair apparatus 110 is controlled by the repair main control unit 190. The repair main control unit 190 includes a repair position counter 195 and a repair storage section 197. These elements are substantially identical to the position counter 95 and the storage section 97 of the manufacturing apparatus 100, except that the repair portions, which are identified by the repair portion identifying section 96 and then stored in the storage section 97 of the manufacturing apparatus 100, are transmitted to the repair storage section 197.

The repair apparatus 110 for the organic EL element includes a dispenser 160 for partition wall repair, a laser zapping apparatus 170, a repair droplet applying apparatus 120G for a gate, a repair droplet applying apparatus 120I for an insulating layer, a repair droplet applying apparatus 120SD for source, drain and pixel electrode, a repair cutting apparatus 130, a repair droplet applying apparatus 120OS for organic semiconductor, and a remover 115. Since the repair droplet applying apparatus 120 and the repair cutting apparatus 130 are equal to the droplet applying apparatus 20 and the cutting apparatus 30 of the manufacturing apparatus 100, details thereof will be omitted.

The dispenser 160 for the partition wall repair applies ultraviolet-curable resin HR having a high viscosity. The ultraviolet-curable resin HR is applied on the sheet substrate FB through nozzles of the dispenser 160 for the partition wall repair by air pressure and the like, so that partition walls BA of the ultraviolet-curable resin HR are formed. The partition walls BA of the ultraviolet-curable resin HR formed on the sheet substrate FB are cured by an ultraviolet lamp 165 such as a mercury lamp.

If the partition walls BA are repaired, the metal ink MI or the like is applied by the repair droplet applying apparatus 120G for the gate and the like, so that the organic EL element 50 is repaired. The remover 115 is provided for the final process of the repair apparatus 110 for the organic EL element. The remover 115 removes a portion where the partition wall BA protrudes higher the design value as a result of the imprinting, or removes the portions where the cured ultraviolet-curable resin HR protrudes higher than the design value, or removes the metal ink MI applied on a portion different from an originally designed portion. In detail, the defective portion is sublimated by a laser or cut away by a knife 117.

In the repair apparatus 110 for the organic EL element, the wind-up roll RE of the manufacturing apparatus 100, which wounds the sheet substrate FB in a roll shape in the final process, is mounted on a repair supply roll FRL. Therefore, the repair apparatus 110 feeds the sheet substrate FB in the −X-axis direction which is reverse to the +X-axis direction which is traveling direction of the manufacturing apparatus 100. That is, the repair apparatus 110 feeds the sheet substrate FB from the termination to a beginning direction of the wind-up roll RE which is wound in the manufacturing apparatus 100, and the sheet substrate FB is wound onto a repair wind-up roll FRE.

In the repair supply roll FRL and the repair wind-up roll FRE, the variation of speed can be significantly increased as compared with the supply roll RL and the wind-up roll RE of the manufacturing apparatus 100. If a plurality of repair portions exist in the range of 102 meters to 105 meters from the termination of the sheet substrate FB having a length of 200 meters or more, the repair supply roll FRL and the repair wind-up roll FRE are rotated to the vicinity of 102 meters from the termination at a high speed and then rotated at a low speed, so that the sheet substrate FB is moved to the repair portions which exist in the distance of 102 meters from the termination. Consequently, the repair apparatus 110 performs such an operation to shorten the repair time required in the batch processing.

An eleventh alignment sensor CA11 is provided downstream of the −X-axis direction of the repair supply roll FRL. The eleventh alignment sensor CA11 detects the first marks AM and the second marks BM. When the repair portions exist in the range of 102 meters to 105 meters from the termination of the sheet substrate FB having a length of 200 meters or more, the sheet substrate FB is feed at a high speed. Thus, the repair main control unit 190 confirms the feed position of the sheet substrate FB based on the image signal of the second marks BM provided for each row of the organic EL element 50. Then, if the repair portions are approaching, the sheet substrate FB is feed to the row number of the organic EL element 50 where the repair portion is located by using the first marks AM.

In the final process of the repair apparatus 110, the eleventh monitoring apparatus CH11 is provided to check whether the repair process has been completely performed. It is also possible for an eleventh monitoring apparatus CH11 to be provided not only in the final process, but in each repair process.

In FIG. 9A, description regarding the repair process after the droplet applying apparatus 20 for the light emitting layer is omitted. However, it is of course possible to also provide a repair droplet applying apparatus 120 for a light emitting layer.

Figure 9B:
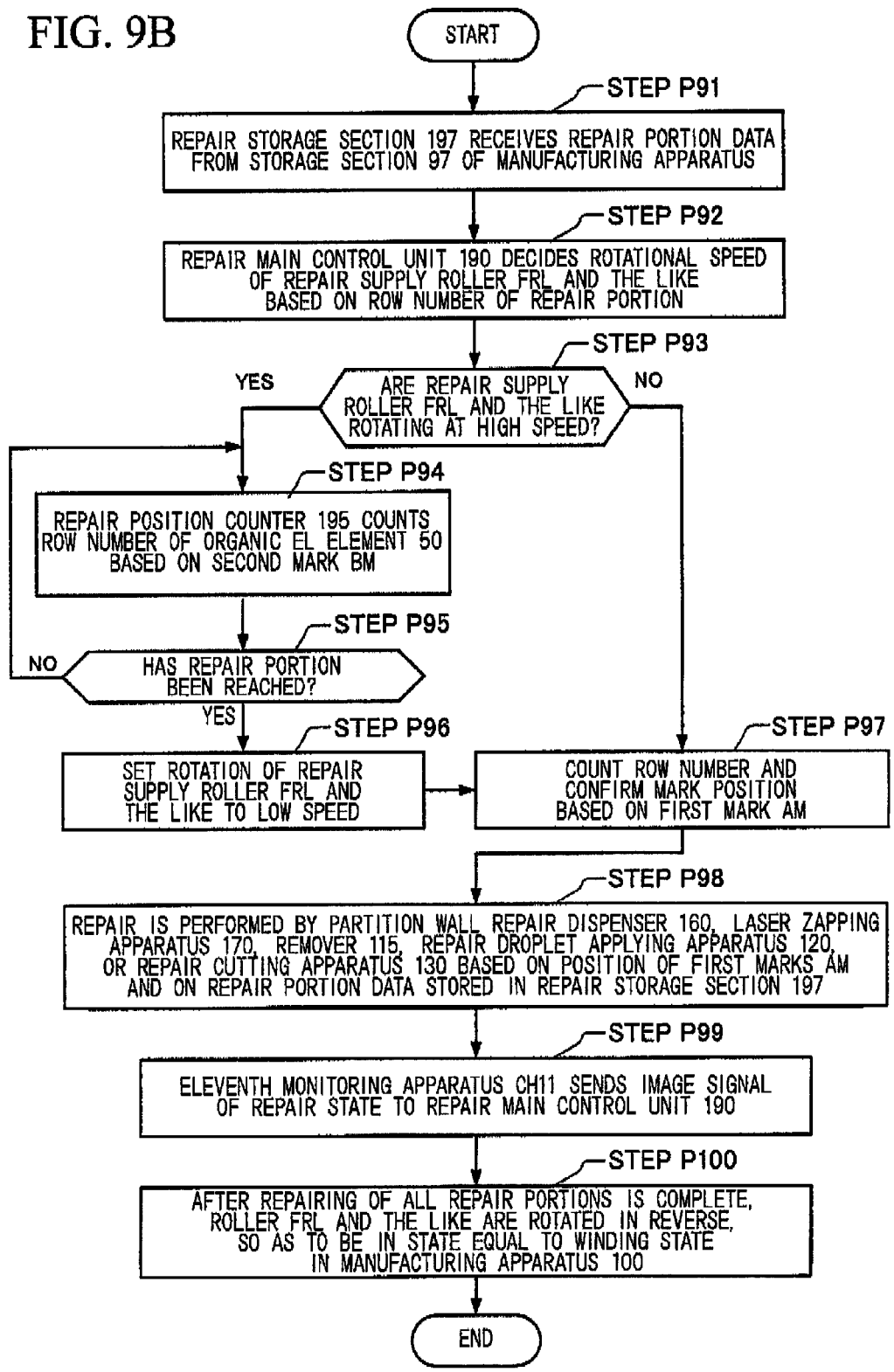
FIG. 9B is a repair flowchart of a repair apparatus 110 in relation to a batch processing illustrated in FIG. 9A.

FIG. 9B is a repair flowchart illustrating the repair apparatus 110 that performs the batch processing illustrated in FIG. 9A.

In Step P91, the repair storage section 197 receives data regarding repair portions from the storage section 97 of the manufacturing apparatus 100. Thus, the repair main control unit 190 ascertains the repair portions where repairs need to be made.

In Step P92, the repair main control unit 190 decides the rotational speed of the repair supply roll FRL and the like based on the row number of the repair portions. For example, if the repair portions are located adjacent to the termination of the wind-up roll RE which is wound in the manufacturing apparatus 100, the repair main control unit 190 decides the repair supply roll FRL and the like to rotate at a low speed. However, if the repair portions are located far from the termination of the wind-up roll RE, the repair main control unit 190 decides the repair supply roll FRL and the like to rotate at a high speed. As described above, control of the rotational speed results in shortening of the movement time to the repair portions. The repair main control unit 190 feeds the sheet substrate FB at the decided rotational speed in the −X-axis direction.

In Step P93, the repair main control unit 190 determines whether the repair supply roll FRL and the like is rotated at a high speed. If they are rotated at a high speed, then proceeds to Step P94. However, if they are rotated at a low speed, then proceeds to Step P97.

In Step P94, the repair position counter 195 counts the row number of the organic EL element 50 based on the first mark AM and the second mark BM shown in FIG. 2. In the counting of the row number, the row number gradually decreases because the sheet substrate FB is moved in the –X-axis direction.

In Step P95, the repair main control unit 190 determines whether the repair portions are approaching based on the counting result of the row number by the repair position counter 195. If the repair portions are approaching, then proceeds to Step P96. However, if the repair portions are not approaching, then returns to Step P94.

In Step P96, the repair main control unit 190 sets the repair supply roll FRL and the like to rotate at a low speed. Further, the repair main control unit 190 selects a repair apparatus based on the data regarding repair portions stored in the repair storage section 197, and moves the repair apparatus in advance in the Y direction of the defects. In this way, the correction time can be shortened.

Next, in Step P97, the row number is counted based on the first mark AM and the position is confirmed using the first mark AM as an alignment mark. The repair main control unit 190 confirms tilt or shift of the sheet substrate FB in the Y-axis direction.

In Step P98, the position of the repair apparatus 110 is adjusted in one or both of X and Y directions, and the defective portions of the organic EL element 50 are repaired based on the position of the first mark AM and the repair portion data stored in the repair storage section 197. If the partition wall BA is defective, then the partition wall repair dispenser 160, the laser zapping apparatus 170 or the remover 115 repairs the defective portions thereof. If defective applying of the metal ink MI occurs in the pixel region, the laser zapping apparatus 170 removes the defective metal ink MI and the repair droplet applying apparatus 120SD newly applies metal ink MI. As described above, the repair main control unit 190 appropriately selects a repair process according to the defect contents of the repair portions. A plurality of the same repair apparatuses are provided so that movement in the Y direction can be reduced or removed (canceled). In addition, the repairs can be performed at the same time.

In Step P99, the eleventh monitoring apparatus CH11 sends an image signal regarding the repair state to the repair main control unit 190. Further, the eleventh monitoring apparatus CH11 confirms whether the repair portions are completely recovered.

If all repair portions have been completely repaired, the roller FRL and the like is set to be rotated in the reverse direction so as to be in a state equal to the winding state in the manufacturing apparatus 100 (P100).

The feeding speed of the sheet substrate FB by the repair supply roll FRL is divided into two stages, that is, a low speed and a high speed. However, speed variation of three stages or more may be accomplished. It is preferable for the speed control to be a type of feedback control such as PID control or the like.

Further, in the above flowchart, the repair apparatus 110 confirms the first mark AM and the second mark BM and performs the repair process during the movement of the sheet substrate FB in the –X-axis direction. However, the repair apparatus 110 may also perform the repair process during the movement of the sheet substrate FB in the X-axis direction after completely moving the sheet substrate FB in the –X-axis direction.

<<Manufacturing and Repair Apparatus for Organic EL Element>>

Figure 10:
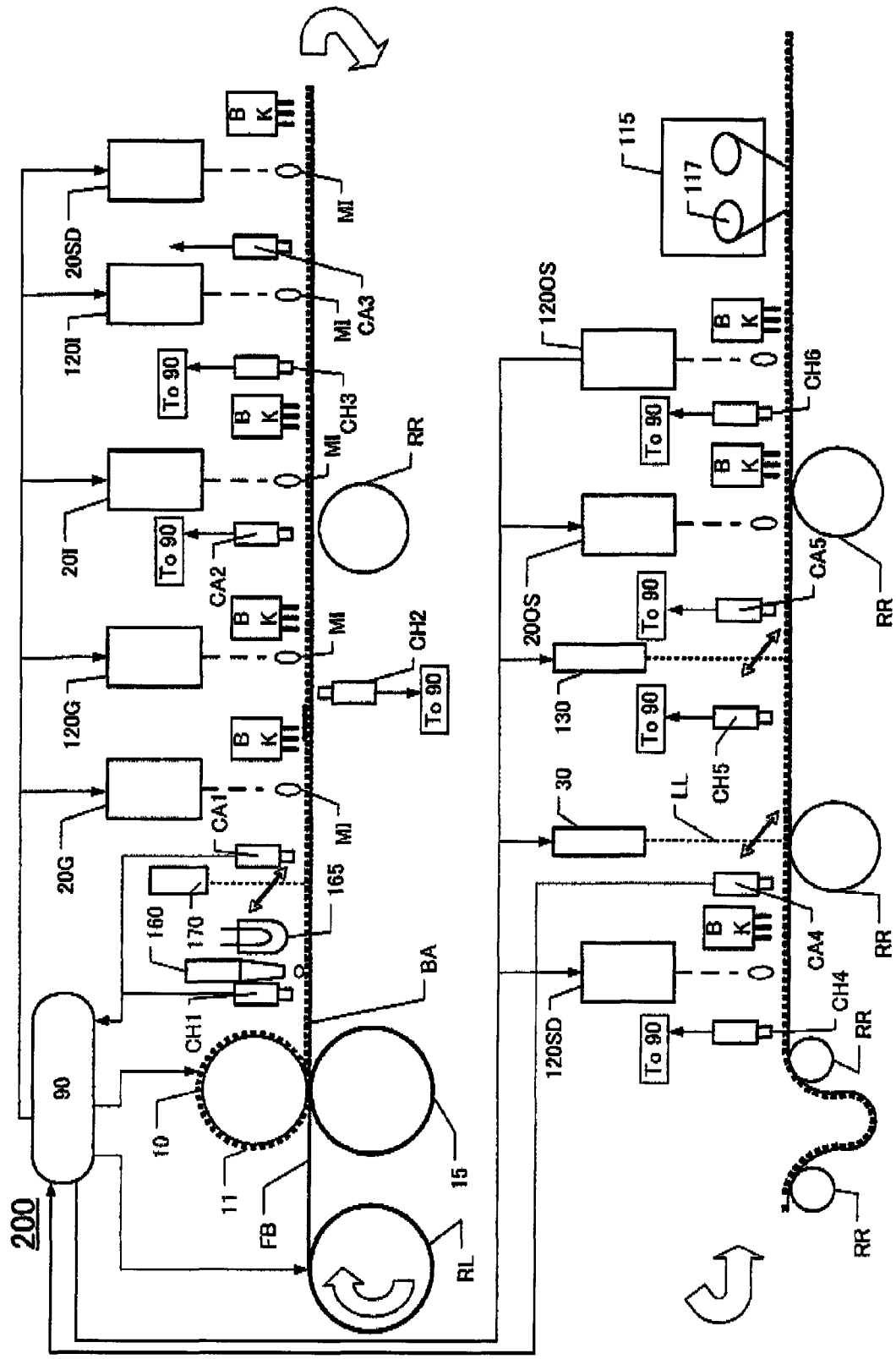
FIG. 10 is a schematic view showing a manufacturing and repair apparatus 200 that monitors defective portions while manufacturing an organic EL element 50, and repairs the defective portions in line.

FIG. 10 is a schematic view showing a manufacturing and repair apparatus 200 that monitors defective portions while manufacturing the organic EL element 50, and repairs the defective portions in line when defective portions have occurred. Note that, processes after the light emitting layer process are not shown in FIG. 10. Further, in FIG. 10, the same reference numerals are used to designate the same elements as those of the manufacturing apparatus 100 shown in FIG. 1 or the repair apparatus 110 shown in FIG. 9A.

The sheet substrate FB which has been fed from the supply roll RL is pressed by the imprint roller 10, and the sheet substrate FB is heated by the thermal transfer roller 15 to a glass transition point or more such that the shape of the pressed partition walls BA is maintained.

The first monitoring apparatus CH1, the partition wall repair dispenser 160, and the laser zapping apparatus 170 are provided downstream of the X-axis direction of the imprint roller 10. The repair droplet applying apparatus 120G for the gate is provided downstream of the laser zapping apparatus 170. The first monitoring apparatus CH1 monitors whether the partition walls BA for the wiring of the thin film transistor and the display pixel have been accurately formed. If defective portions are found in the partition walls BA by the first monitoring apparatus CH1, the partition wall repair dispenser 160 applies ultraviolet-curable resin HR on the sheet substrate FB. Then, the resin cured by using an ultraviolet lamp 144 and the partition walls BA of the defective portions is repaired. Further, if extra partition walls BA have been formed, the laser zapping apparatus 170 removes the extra partition walls BA. The first alignment sensor CA1 is provided downstream of the laser zapping apparatus 170.

After the first mark AM and the second mark BM are detected by the first alignment sensor CA1, the sheet substrate FB is subject to an electrode formation process.

In the electrode formation process, the gate droplet applying apparatus 20G receives position information from the first alignment sensor CA1 and applies the metal ink MI in the groove GR between the partition walls BA of the gate bus line GBL. Then, the metal ink MI is dried or baked by the heat treatment apparatus BK.

The second monitoring apparatus CH2 is provided downstream of the gate droplet applying apparatus 20G, and the repair droplet applying apparatus 120G for the gate is provided downstream of the second monitoring apparatus CH2. The second monitoring apparatus CH2 monitors whether the metal ink MI has been applied on the gate bus line GBL and serves as a conductive line. If defective portions are found in the gate bus line GBL by the second monitoring apparatus CH2, the repair droplet applying apparatus 120G for the gate applies the metal ink MI on the sheet substrate FB. The second alignment sensor CA2 is provided downstream of the repair droplet applying apparatus 120G for the gate.

Also in the case of the insulating layer droplet applying apparatus 20I and the like, a monitoring process is performed after a manufacturing process and defective portions are repaired in a repair process if they are found in the monitoring process. Further, in the manufacturing and repair apparatus 200 shown in FIG. 10, the remover 115 is provided after the organic semiconductor droplet applying apparatus 20OS. However, plural remover 115 may be provided after the imprint roller 10, or after each droplet applying apparatus 20 or the like.

In addition, the manufacturing time of the organic EL element 50 does not always coincide with the repair time of defective portion in the same process. Moreover, the imprint process or each applying process is not completed in the same time. Therefore, when in-line manufacturing or repair is performed, the supply roller RL and the like must be rotated according to the speed of a process requiring much more time. However, since the productivity cannot be increased under such circumstances, if the process requiring much more time is a process in which the remover 115 removes the defective portion, then productivity can be raised as much as possible by providing two removers 115, or by allowing the sheet body FB to be hang loosely as shown in the lower left end of FIG. 10, resulting in an increase in productivity.

INDUSTRIAL APPLICABILITY

The manufacturing apparatus and the repair apparatus for the organic EL element have been described. However, the manufacturing apparatus and the repair apparatus can also be applied to field emission displays, liquid crystal display elements and the like. In the present embodiment, the thin film transistor using the organic semiconductor has been described. However, a thin film transistor of an amorphous silicon-based inorganic semiconductor may also be employed.

Further, the heat treatment apparatus BK is provided for the manufacturing apparatus 100, the repair apparatus 110 and the manufacturing and repair apparatus 200 of the embodiment. However, with the improvement of metal ink MI, light emitting layer solvents and the like, ink or solvents which do not require heat treatment has been proposed. In this regard, it is not always necessary to provide the heat treatment apparatus BK in the present embodiment.

What is claimed is:

1. A defect detection method of a display device, comprising:
   a defect counting process that measuring a feature amount for each partial region of the display device, and counting a region which is determined as a defective region based on the measured feature amount of a region;
   a process that stopping a manufacturing line of the display device when a number of defects obtained in the defect counting process is greater than a first threshold value;
   a defect density calculating process that calculating a defect density in a predetermined area when the number of defects obtained in the defect counting process is smaller than the first threshold value; and
   a process that stopping the manufacturing line of the display device when the defect density obtained in the defect density calculating process is greater than a second threshold value.

2. The defect detection method according to claim 1, comprising:
   a process that repairing the display device in a repair line when the defect density obtained in the defect density calculating process is smaller than the second threshold value.

3. The defect detection method according to claim 2, wherein
   a defect data which includes a measured position information and a feature amount is transmitted to the repair line, when the display device is sent to the repair line.

4. The defect detection method according to claim 3, wherein
   the display device is formed on a roll shaped flexible substrate, and the flexible substrate is fed at a predetermined speed in the row direction and wound in a roll shape in the manufacturing line; and
   in the repair line, the defective region of the display device which is fed from a state being wound in the roll shape is repaired based on the defect data.

5. A defect detection apparatus of a display device, comprising:
   a defect number determining section that measures a feature amount for each partial region of the display device, and counts a number of defects in a partial region which is determined as a defective region based on the measured feature amount of the partial region, and determines whether the number of defects is greater than a first threshold value; and
   a defect density determining section that calculates the number of defects existing in a predetermined area when the defect number determining section determines that the number of defects is smaller than the first threshold value, and determines whether the number of defects existing in the predetermined area is greater than a second threshold value.

6. The defect detection apparatus according to claim 5, comprising:
   a position counter that identifies a position of the defective region, and outputs the position as position information; and
   a storage section that stores a defect data which includes the position information and the feature amount of a region which is determined as the defective region.

7. A defect detection apparatus of a display device, comprising:
   a defect density determining section that measures a feature amount for each partial region of the display device, counts a number of defects in the partial region which is determined as a defective region based on the measured feature amount of the partial region, calculates the number of defects existing in a predetermined area if the number of defects in the partial region of the display device is smaller than a first threshold value, and determines whether the number of defects existing in the predetermined area is greater than a second threshold value.

8. The defect detection apparatus according to claim 7, wherein the display device comprises a plurality of pixel areas defined by a plurality of partition walls, and the feature amount comprises at least one of a height of the partition wall, a position of the partition wall, and a gap between electrodes of the display device.

9. The defect detection apparatus according to claim 8, wherein the partial region comprises a plurality of subdivided partial regions which are arranged in a matrix of rows and columns.

10. The defect detection apparatus according to claim 9, wherein the number of defects in the partial region is counted as a number of the subdivided partial regions including the defect.

11. The defect detection apparatus according to claim 10, wherein the predetermined area is determined by the subdivided partial regions arranged in row and column directions of the matrix.

* * * * *

UNITED STATES PATENT AND TRADEMARK OFFICE
CERTIFICATE OF CORRECTION

PATENT NO. : 8,301,289 B2  Page 1 of 1
APPLICATION NO. : 12/753517
DATED : October 30, 2012
INVENTOR(S) : Kei Nara and Tomohide Hamada It is certified that error appears in the above-identified patent and that said Letters Patent is hereby corrected as shown below:

On the Title Page, item [57]:

Abstract, Line 2, "measuring" should read as --measures--.

Abstract, Line 3, "counting" should read as --counts--.

Abstract, Line 6, "stopping" should read as --stops--.

Abstract, Line 9, "calculating" should read as --calculates--.

Abstract, Line 12, "stopping" should read as --stops--.

In the Claims:

Claim 1, Col. 21, Line 35, "measuring" should read as --measures--.

Claim 1, Col. 21, Line 36-37, "counting" should read as --counts--.

Claim 1, Col. 21, Line 39, "stopping" should read as --stops--.

Claim 1, Col. 21, Line 42, "calculating" should read as --calculates--.

Claim 1, Col. 21, Line 46, "stopping" should read as --stops--.

Claim 2, Col. 21, Line 52, "repairing" should read as --repairs--.

Signed and Sealed this
Thirtieth Day of April, 2013

Teresa Stanek Rea
*Acting Director of the United States Patent and Trademark Office*